(12) United States Patent
Hashino et al.

(10) Patent No.: US 8,439,886 B2
(45) Date of Patent: May 14, 2013

(54) ABSORBENT ARTICLE

(75) Inventors: Akira Hashino, Kagawa (JP); Jun Kudo, Kagawa (JP); Hideyuki Kinoshita, Kagawa (JP)

(73) Assignee: Uni-Charm Corporation, Shikokuchuo-Shi, Ehime (JP)

( * ) Notice: Subject to any disclaimer, the term of this patent is extended or adjusted under 35 U.S.C. 154(b) by 495 days.

(21) Appl. No.: 12/593,710

(22) PCT Filed: Jan. 25, 2008

(86) PCT No.: PCT/JP2008/051103
§ 371 (c)(1),
(2), (4) Date: Jan. 8, 2010

(87) PCT Pub. No.: WO2008/126439
PCT Pub. Date: Oct. 23, 2008

(65) Prior Publication Data
US 2010/0121302 A1 May 13, 2010

(30) Foreign Application Priority Data

Mar. 30, 2007 (JP) ................. 2007-093744

(51) Int. Cl.
*A61F 13/15* (2006.01)
*A61F 13/20* (2006.01)
(52) U.S. Cl.
USPC ............ 604/385.01; 604/385.16; 604/385.24
(58) Field of Classification Search ............ 604/385.01, 604/385.03, 385.101, 385.11, 385.16, 385.201, 604/385.24
See application file for complete search history.

(56) References Cited

U.S. PATENT DOCUMENTS

| 6,464,677 | B1 | 10/2002 | Noguchi et al. |
| 6,632,211 | B2 | 10/2003 | Otsubo |
| 6,676,649 | B2 | 1/2004 | Mizutani |
| 2001/0016720 | A1 | 8/2001 | Otsubo |
| 2002/0143309 | A1 | 10/2002 | Glasgow et al. |

(Continued)

FOREIGN PATENT DOCUMENTS

| CN | 1224606 | 8/1998 |
| EP | 0 933 073 A2 | 8/1999 |

(Continued)

OTHER PUBLICATIONS

PCT/JP2008/051103 International Search Report.

(Continued)

*Primary Examiner* — Michele M Kidwell
(74) *Attorney, Agent, or Firm* — Lowe Hauptman Ham & Berner, LLP

(57) ABSTRACT

An absorbent article adapted to be worn by a user includes a main body section and an absorbent body that has an absorbent member for absorbing fluid, that has a longitudinal direction, a width direction, and a thickness direction, that is superposed on a face of the main body section on a user side. The absorbent body further has one end section in the longitudinal direction joined to the main body section on a first joined section, and another end section in the longitudinal direction joined to the main body section on a second joined section. A length of the absorbent body between the first joined section and the second joined section is equal to or more than a length of the main body section between the first joined section and the second joined section.

18 Claims, 16 Drawing Sheets

U.S. PATENT DOCUMENTS

| | | | |
|---|---|---|---|
| 2006/0282059 A1 * | 12/2006 | Fujikawa et al. | ........ 604/385.17 |
| 2009/0306618 A1 | 12/2009 | Kudo et al. | |
| 2010/0076392 A1 | 3/2010 | Kudo | |
| 2010/0145296 A1 | 6/2010 | Kudo et al. | |

FOREIGN PATENT DOCUMENTS

| | | | |
|---|---|---|---|
| EP | 0985396 A2 | | 3/2000 |
| EP | 1 080 708 A2 | | 3/2001 |
| EP | 1245211 A2 | | 2/2002 |
| EP | 2042140 A1 | | 1/2009 |
| EP | 2044914 A1 | | 8/2009 |
| EP | 2092917 A1 | | 8/2009 |
| JP | 11-104168 A | | 4/1999 |
| JP | 11-206809 A | | 8/1999 |
| JP | 2001-061885 A | | 3/2001 |
| JP | 2002-159534 | * | 6/2002 |
| WO | 02/062278 | * | 8/2002 |

OTHER PUBLICATIONS

European extended search report dated Dec. 1, 2011.
Australian Office Action for Application No. 2008238675 mailed Aug. 2, 2012.

* cited by examiner

A-A CROSS SECTION

B-B CROSS SECTION

C-C CROSS SECTION

A-A CROSS SECTION

WIDTH DIRECTION ↔

SURFACE SIDE ↑ THICKNESS DIRECTION ↓ BACK FACE SIDE

B-B CROSS SECTION

C-C CROSS SECTION

D-D CROSS SECTION

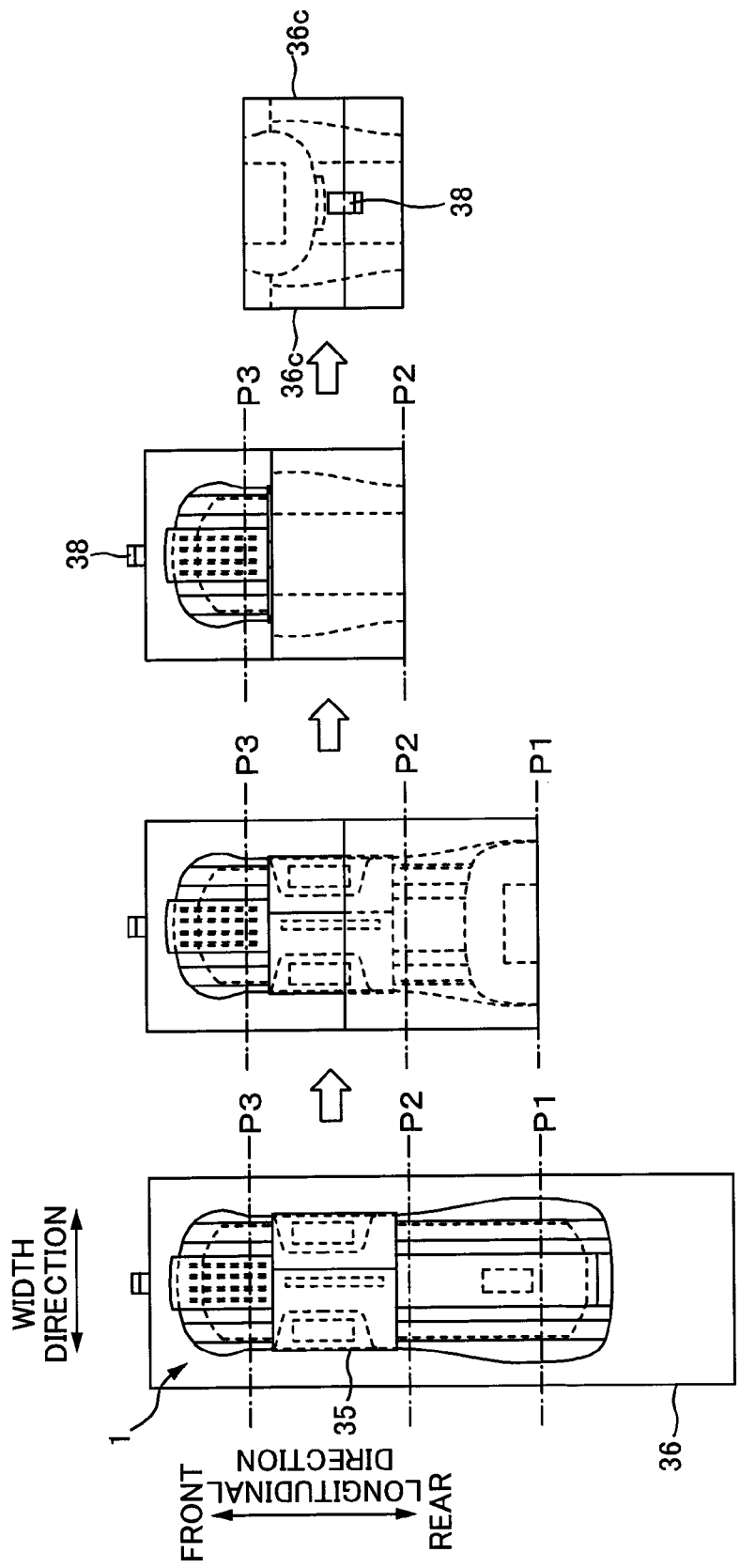

NAPKIN 1 OF PRESENT EMBODIMENT
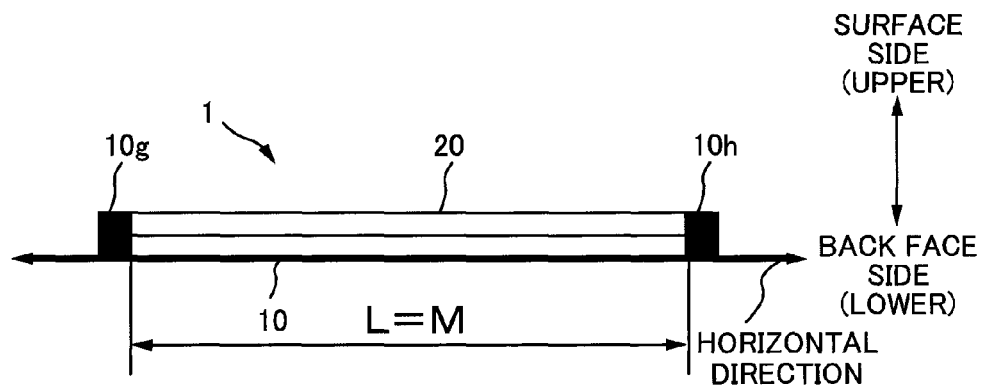
NAPKIN 2 OF COMPARATIVE EXAMPLE
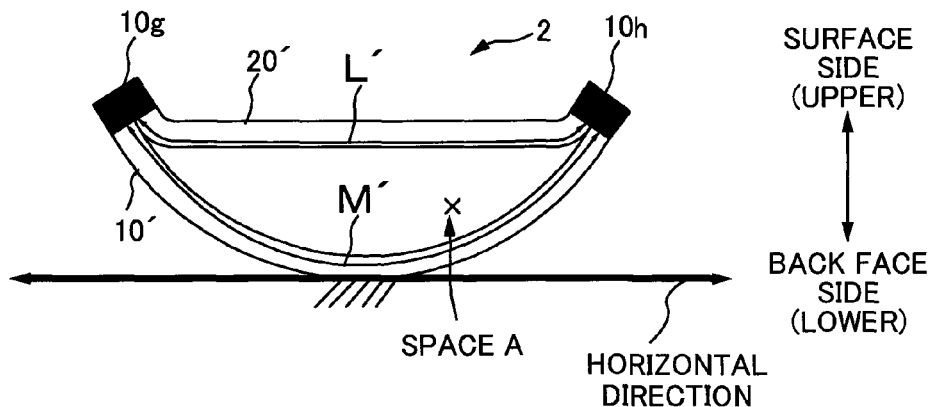
FIG. 12

ABSORBENT ARTICLE

RELATED APPLICATIONS

The present application is based on International Application PCT/JP2008/051103, filed Jan. 25, 2008, which claims priority from, Japan Application Number 2007-093744, filed Mar. 30, 2007, the disclosures of which are hereby incorporated by reference herein in their entirety.

TECHNICAL FIELD

The present invention relates to an absorbent article for absorbing fluid.

BACKGROUND ART

Conventionally, absorbent articles have been known that include an absorbent body for absorbing a certain fluid such as menstrual blood. Some of the absorbent articles have, for example, a two-layer structure including an upper layer section that absorbs fluid and a lower layer section that is overlapped with the upper layer section. In addition, an absorbent article has been proposed in which the upper layer section is coupled via a longitudinally stretchable elastic member to the lower layer section and separates upwards from the lower layer section in a natural state (unstressed state) in order to improve the fitting property of the upper layer section to the groove of user's body (see JP-A-H11-104168, for example).

DISCLOSURE OF INVENTION

Problem to be Solved by the Invention

The user of an absorbent article usually adhesively fixes a back face of the absorbent article to an inner face of an undergarment being away from the body, then pulls up the undergarment toward the body, and wears the absorbent article. Thus, with the absorbent article having a two-layer structure as described above, since the lower layer section (main body section) is curved with respect to the upper layer section (absorbent body) in a natural state, adhesive fixing of the back face of the lower layer section to the inner face of the undergarment becomes unstable, resulting in a problem that it is difficult for the user to wear the absorbent article.

The invention has been made in view of conventional problems as described above, and an advantage thereof is to provide an absorbent article that can be easily worn.

Means for Solving the Problem

In order to solve the above-described problem, a main aspect of the invention is directed to an absorbent article that is worn by a user, including: a main body section of the absorbent article; and an absorbent body
that has an absorbent member absorbing fluid,
that has a longitudinal direction, a width direction, and a thickness direction,
that is superposed on a face of the main body section on a user side,
whose one end section in the longitudinal direction is joined to the main body section on a first joined section, and
whose another end section in the longitudinal direction is joined to the main body section on a second joined section, wherein a length of the absorbent body between the first joined section and the second joined section is equal to or more than a length of the main body section between the first joined section and the second joined section.

Effects of the Invention

According to the invention, it is possible to provide an absorbent article that can be easily worn.

BRIEF DESCRIPTION OF DRAWINGS

FIGS. 9A to 9D are explanatory views of the manner in which the sanitary napkin is wrapped.
FIG. 12 is a schematic view of cross sections of the sanitary napkin of the present embodiment and a sanitary napkin of a comparative example.

LIST OF REFERENCE NUMERALS

Figure 1:
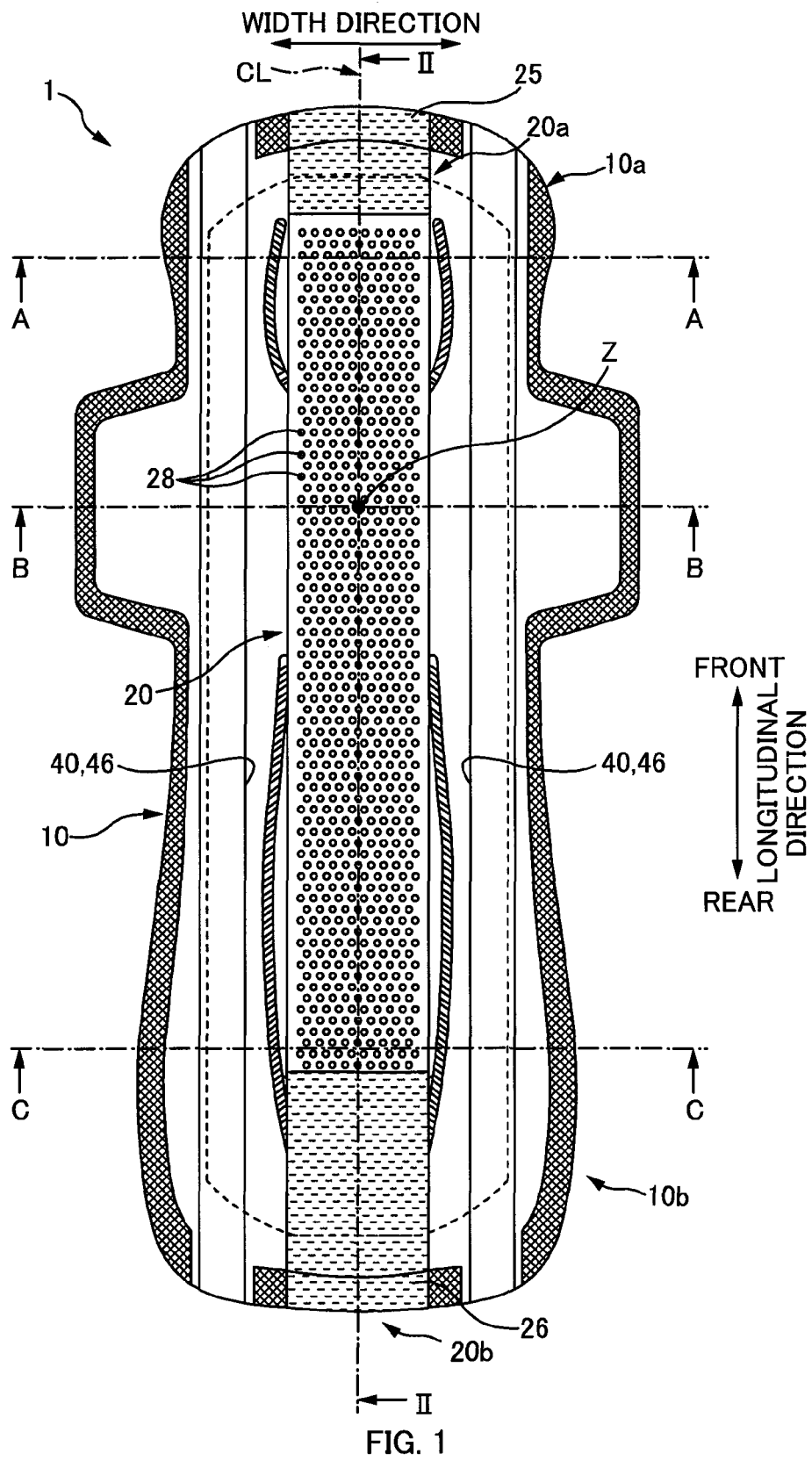
FIG. 1 is a plan view of the surface side of a sanitary napkin in an opened state.

1 . . . sanitary napkin (absorbent article), 2 . . . sanitary napkin of a comparative example, 3 . . . sanitary napkin of a modified example, 10 . . . base absorbent body (main body section), 10*a* . . . front end section, 10*b* . . . rear end section, 12 . . . absorbent body base material, 12*a* . . . pulverized pulp layered body, 10*e* . . . rear extremity edge, 10*g* . . . first joined section, 10*h* . . . second joined section, 14 . . . surface sheet, 20 . . . top absorbent body (absorbent body), 20*a* . . . front end section, 20*b* . . . rear end section, 22 . . . pulverized pulp layered body (absorbent member), 23 . . . intermediate sheet, 24 . . . shape retaining sheet (surface member), 25 . . . sealed section, 26 . . . sealed section, 27 . . . fastening section, 28 . . . perforation, 30 . . . back face sheet, 31 . . . anti-displacement affixing section, 32 . . . holding section, 33 . . . anti-displacement affixing section, 34 . . . protection sheet, 35 . . . protection sheet, 36 . . . wrapping sheet, 38 . . . tape, 40 ... side sheet, 44 ... fixed section, 46 ... end section, 48 ... elastic member, 51 ... leakage-proof sheet, 60 ... pick-up section, 90 ... undergarment, CL ... center line, Z ... point that is supposed to face vaginal orifice, L ... absorbent body length, M ... main body section length, Ln ... necessary length, E ... excessive length

BEST MODE FOR CARRYING OUT THE INVENTION

At least the following matters are disclosed in the description of the present specification and the accompanying drawings.

An absorbent article that is worn by a user, including: a main body section of the absorbent article; and an absorbent body
that has an absorbent member absorbing fluid,
that has a longitudinal direction, a width direction, and a thickness direction,
that is superposed on a face of the main body section on a user side,
whose one end section in the longitudinal direction is joined to the main body section on a first joined section, and
whose another end section in the longitudinal direction is joined to the main body section on a second joined section,
wherein a length of the absorbent body between the first joined section and the second joined section is equal to or more than a length of the main body section between the first joined section and the second joined section.

With this absorbent article, in a natural state, it is possible to prevent the absorbent body from separating upwards from the main body section, and to prevent the main body section from curving with respect to the absorbent body. Accordingly, the main body section is substantially flat, and the back face of the main body section is adhesively fixed securely to an inner face of an undergarment of the user. Thus, loose displacement of the absorbent article when the user pulls up the undergarment can be suppressed. In other words, the user can easily wear this absorbent article.

In such an absorbent article, the length of the absorbent body between the first joined section and the second joined section and the length of the main body section between the first joined section and the second joined section are lengths in a state where no force is externally applied to the absorbent article.

With such an absorbent article, the main body section is substantially flat in a state where no force is applied from the outside to the absorbent article (in a natural state), and thus the user can easily wear the absorbent article. Even if the length of the absorbent body between the first joined section and the second joined section is equal to or longer than the length of the main body section between the first joined section and the second joined section in a state where the absorbent article is stretched, when the length of the absorbent body between the first joined section and the second joined section is shorter than the length of the main body section between the first joined section and the second joined section in the natural state, the user has to adhesively fix the back face of the absorbent article to the inner face of the undergarment while stretching the absorbent article by the user's hand, and thus it is difficult for the user to wear the absorbent article.

In such an absorbent article, the length of the absorbent body between the first joined section and the second joined section is equal to the length of the main body section between the first joined section and the second joined section.

With such an absorbent article, the absorbent body and the main body section can be joined in a state where the absorbent body and the main body section are opened flat. Thus, the production process becomes easy. If the length of the absorbent body between the first joined section and the second joined section is longer than the length of the main body section between the first joined section and the second joined section, in the process of joining the main body section and the absorbent body, the absorbent body has to be lifted or to be folded by the amount by which the length of the absorbent body between the first joined section and the second joined section is longer than the length of the main body section between the first joined section and the second joined section.

In such an absorbent article, the absorbent body includes a surface member that covers the absorbent member, the absorbent body includes a sealed section between the first joined section and the second joined section, the sealed section does not contain the absorbent member and has the surface member, and in the case where the user pulls up the absorbent body to a side close to the second joined section when wearing the absorbent article, the sealed section is disposed closer to the second joined section than the first joined section.

With such an absorbent article, since the sealed section does not have an absorbent member, and its rigidity is low, the excessive length of the absorbent body formed when the absorbent body is made to be in close contact with the groove of the user's body can be relieved by being folded up at the sealed section. Furthermore, even if the sealed section is folded up, the thickness is small. Thus, there is formed no gap between other portions, so that an uncomfortable feeling when worn can be suppressed. Moreover, in the case where the absorbent body is pulled up to the side close to the second joined section, the excessive length of the absorbent body formed when the absorbent body is made to be in close contact with groove of the body is folded upon itself at the sealed section on the second joined section side and relieved.

In such an absorbent article, the main body section and the absorbent body are separable from each other between the first joined section and the second joined section, and a fastening section that temporarily joins the main body section and the absorbent body is provided between the sealed section and the first joined section.

With such an absorbent article, the state in which the absorbent body is close contact with the groove of the user's body can be maintained using the fastening section. Furthermore, the portion of the absorbent body on the side closer to the first joined section with respect to the fastening section is pulled up, and thus in a case where the excessive length is formed in the absorbent body, the sealed section on the side closer to the second joined section with respect to the fastening section is folded.

——————Present Embodiment——————

<Brief Configuration of Sanitary Napkin>

Figure 2:
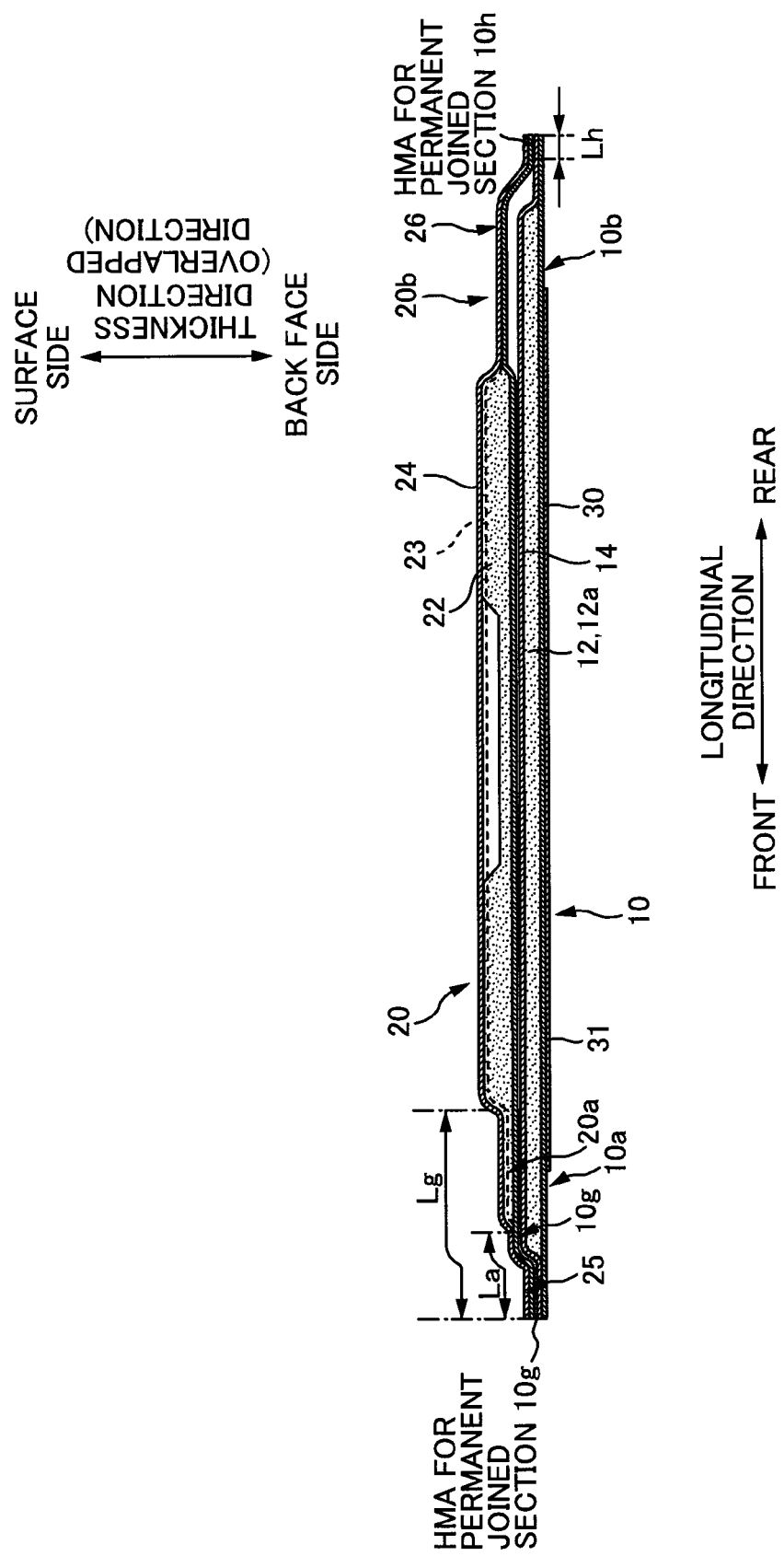
FIG. 2 is a cross-sectional view taken along line II-II in FIG. 1.
Figure 3:
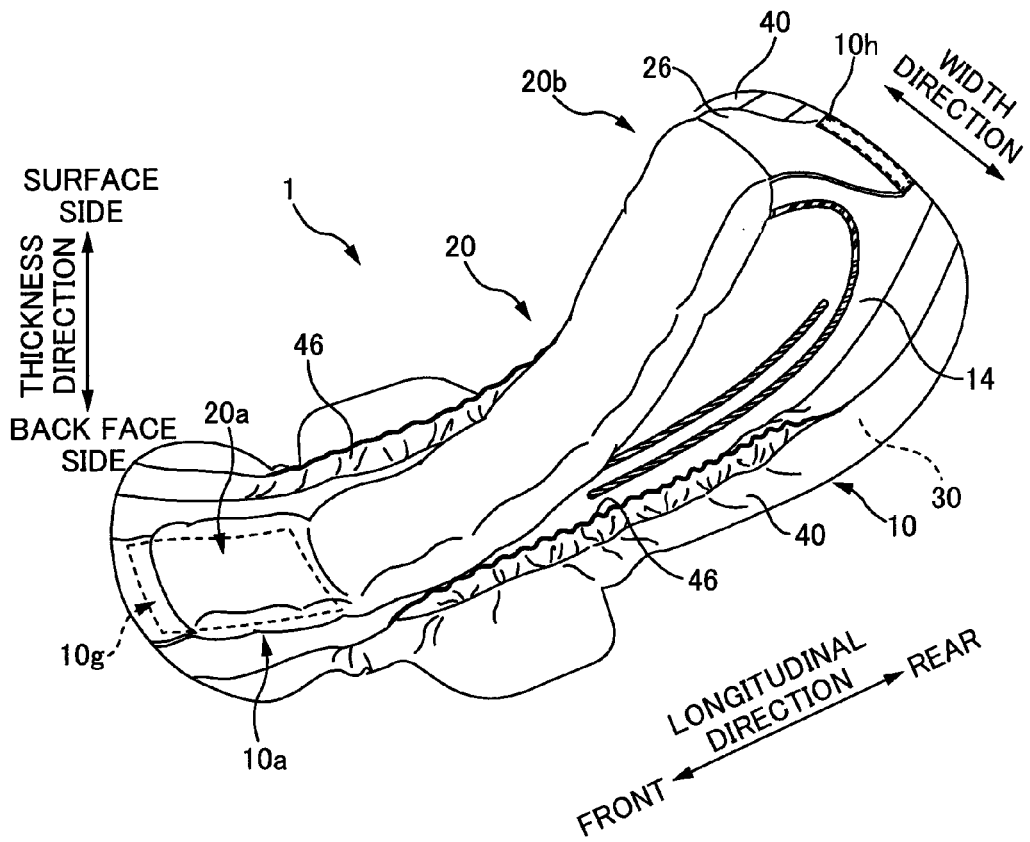
FIG. 3 is a perspective view of the sanitary napkin.

Hereinafter, an absorbent article will be described as a sanitary napkin 1. First, the outline of the configuration of the sanitary napkin 1 of the present embodiment will be described. In the following description, a side that is to be in contact with the body is referred to as a surface side, a side that is to be in contact with an undergarment 90 (garment) is referred to as a back face side, an end section that is positioned on the front side of the body when worn is referred to as a front end section, and an end section that is positioned on the rear side is referred to as a rear end section. Furthermore, a normal direction of the surface or the back face of the sanitary napkin 1 is referred to as a thickness direction. FIG. 1 is a plan view of the surface side of the sanitary napkin 1 in an opened state. FIG. 2 is a cross-sectional view taken along line II-II in FIG. 1. FIG. 3 is a perspective view of the sanitary napkin 1.

The sanitary napkin 1 includes a base absorbent body 10 (corresponding to a main body section), and a top absorbent body 20 (corresponding to an absorbent body) that is superposed on the surface of the base absorbent body 10 and disposed in the longitudinal direction on a center CL in the width direction of the base absorbent body 10. Furthermore, the sanitary napkin 1 is generally elongated in a predetermined direction. In the following description, this predetermined direction is referred to as a longitudinal direction, and the direction that is perpendicular to the longitudinal direction is referred to as a width direction. The longitudinal direction in the worn state corresponds to the fore-and-aft direction of the body.

A front end section 20a and a rear end section 20b of the top absorbent body 20 are undetachably joined respectively to a front end section 10a and a rear end section 10b of the base absorbent body 10. The top absorbent body 20 other than the front end section 20a and the rear end section 20b is separable from the base absorbent body 10.

The user of the sanitary napkin 1 adhesively fixes the back face side of the base absorbent body 10 to the inner face of the undergarment 90 in such a manner that the longitudinal direction is along the fore-and-aft direction of the body. Then, the user pulls up the rear side of the top absorbent body 20 in a state where the undergarment 90 is worn, and wears the sanitary napkin 1 in such a manner as to place the top absorbent body 20 into a groove such as buttocks. Accordingly, fluid such as menstrual blood excreted from the groove is absorbed mainly by the top absorbent body 20.

Note that in the sanitary napkin 1, as shown in FIG. 1, a point Z that is supposed to face the vaginal orifice (corresponding to the bodily discharge opening) is positioned closer to the front side with respect to the middle in the longitudinal direction, on a center line CL with respect to the width direction of the sanitary napkin 1. More specifically, in the sanitary napkin 1, the length from the point Z that is supposed to face the vaginal orifice to the rear side is formed longer than that from the point Z to the front side.

Hereinafter, constituent elements of the sanitary napkin 1 will be described in detail.

<Base Absorbent Body 10>

Figure 4:
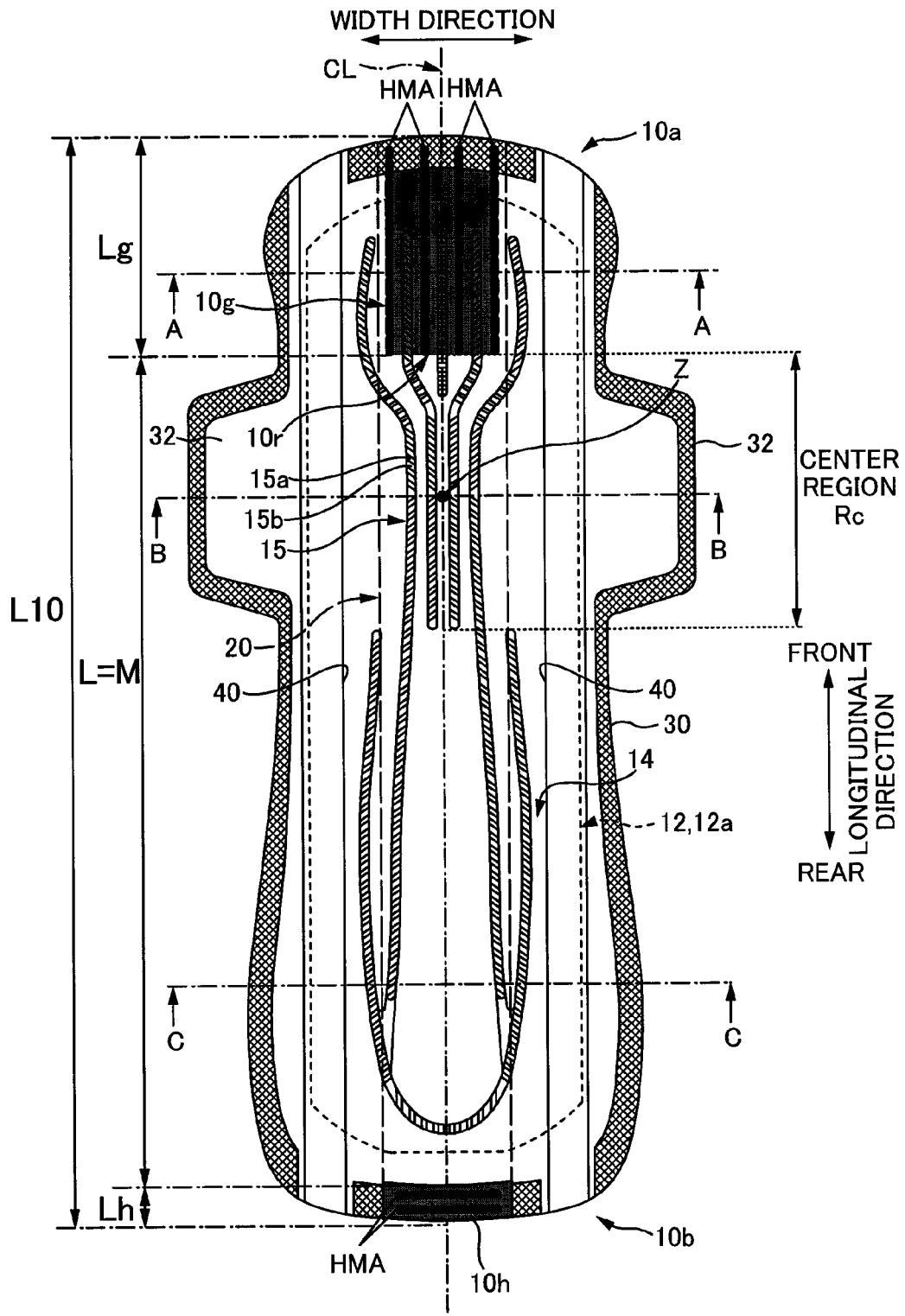
FIG. 4 is a plan view of the surface side of a base absorbent body.
Figure 5:
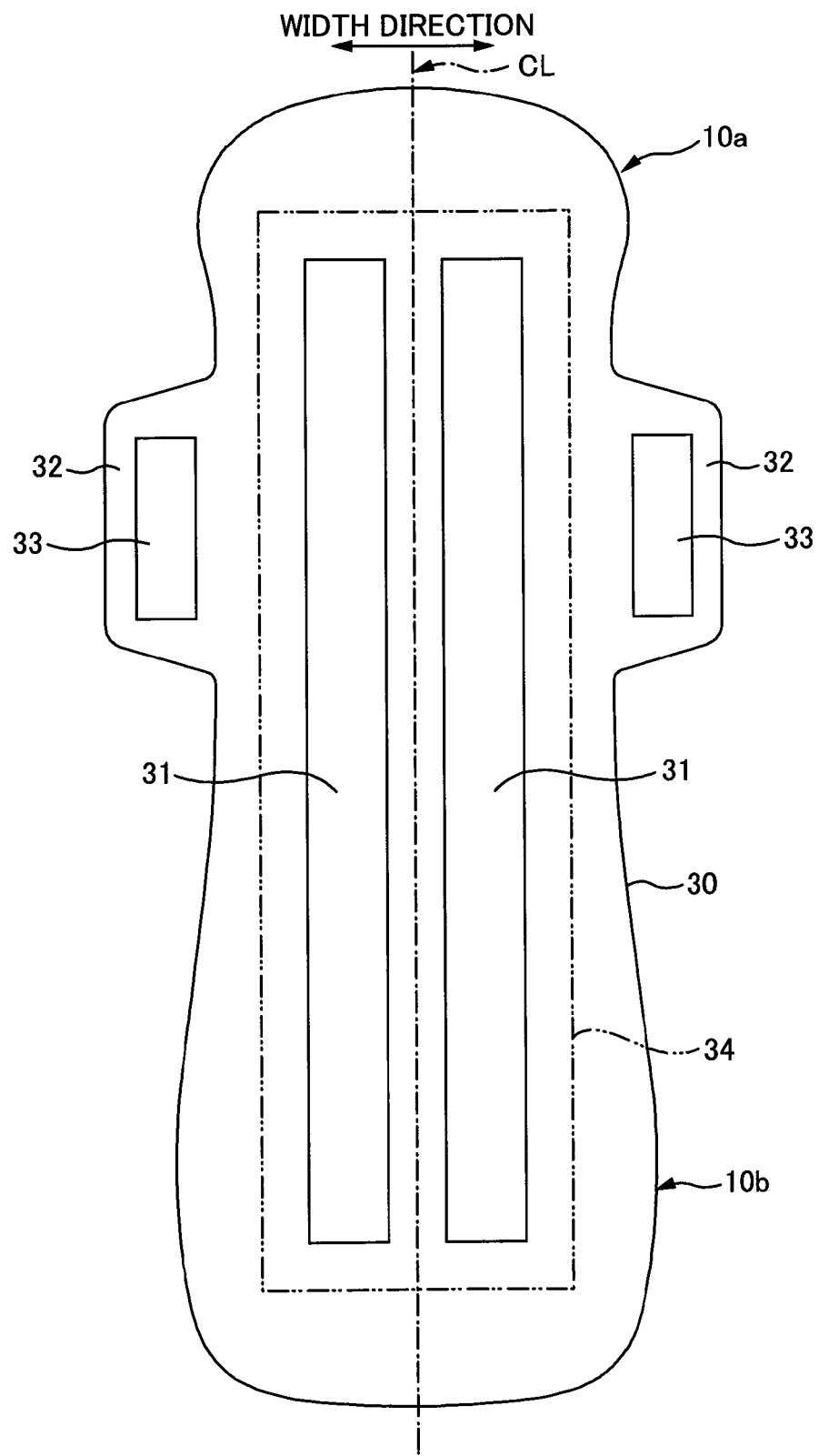
FIG. 5 is a plan view of the back face side of the base absorbent body.
Figure 6A:
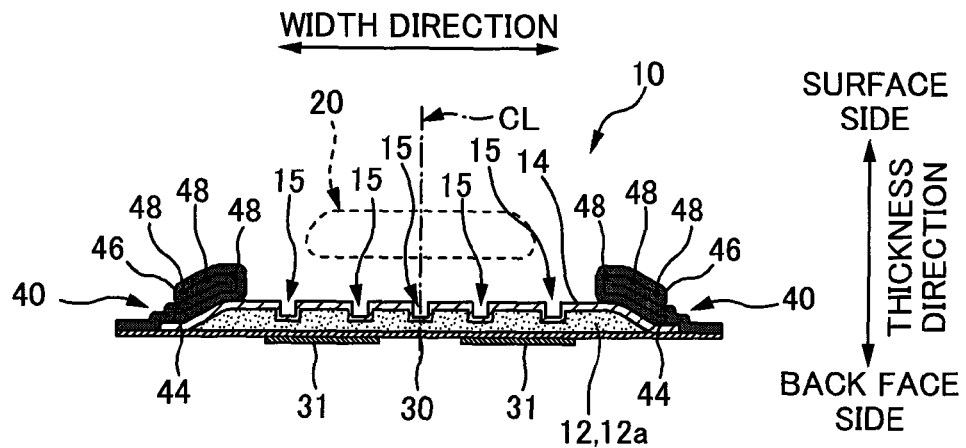
FIGS. 6A to 6C are cross-sectional views respectively taken along lines A-A, B-B, and C-C in FIG. 4.
Figure 6B:
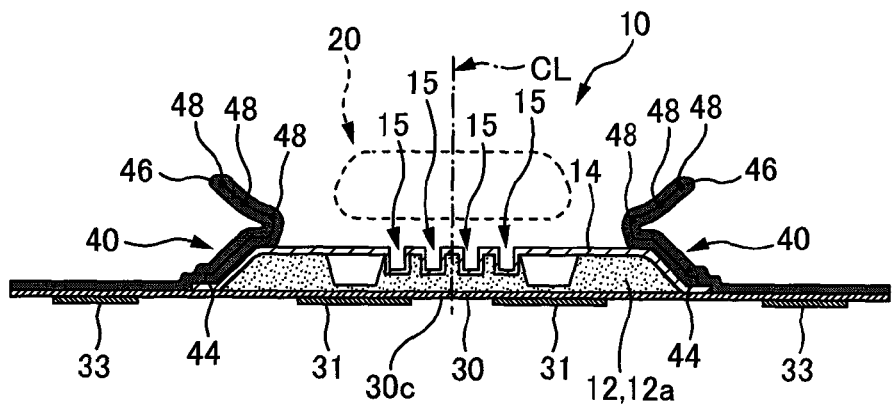
Figure 6C:
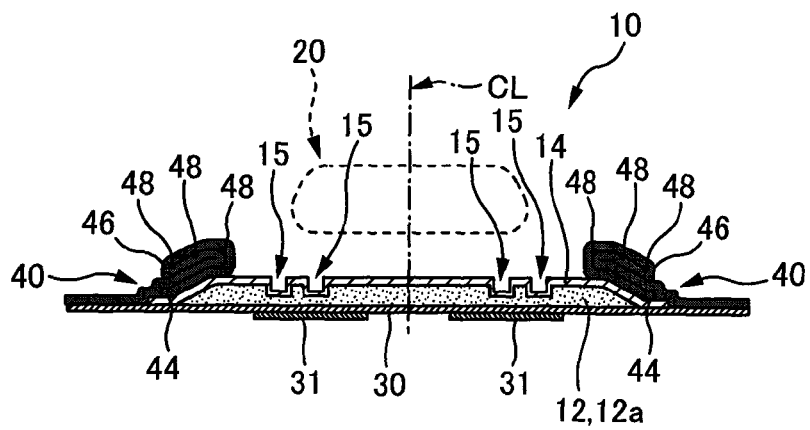

FIG. 4 is a plan view of the surface side of the base absorbent body 10. FIG. 5 is a plan view of the back face side thereof. FIGS. 6A to 6C are cross-sectional views respectively taken along lines A-A, B-B, and C-C in FIG. 4. In FIGS. 4 and 6A to 6C, the top absorbent body 20 is transparent, and only an external shape line thereof is virtually indicated by a dotted line.

When viewed from above, the base absorbent body 10 is a substantial rectangle that is elongated in the longitudinal direction. The base absorbent body 10 has an absorbent body base material 12 that absorbs fluid, a surface sheet 14 that is provided covering at least a surface side of the absorbent body base material 12 throughout, a back face sheet 30 for preventing fluid that has been absorbed in the absorbent body base material 12 from leaking to the back face side, and side sheets 40 for forming leakage-proof walls 46 that prevent fluid from leaking outside in the width direction.

The absorbent body base material 12 has a pulverized pulp layered body 12a in which pulverized pulp obtained by pulverizing pulp is layered, a superabsorbent polymer that is mixed into the pulverized pulp layered body 12a, and a fluid-permeable sheet (not shown) such as tissue paper that covers the pulverized pulp layered body 12a.

The surface sheet 14 is a fluid-permeable sheet. The surface sheet 14 is made of a material such as an appropriate nonwoven fabric; for examples, a through-air nonwoven fabric and a spunlace nonwoven fabric that are formed of synthetic resin fiber such as polyester and polyethylene, on which a hydrophilic treatment or the like has been performed.

Then, the surface sheet 14 and the absorbent body base material 12 are compressed in the thickness direction with having hot-melt adhesive HMA therebetween by a groove embossing process, so that the surface sheet 14 and the absorbent body base material 12 have been joined and integrated. The groove embossing process is performed using a pair of pressing members (not shown) that oppose each other. One pressing member of the pair of pressing members has a continuous rib-shaped protrusion, and on a tip of the rib-shaped protrusion, island-shaped protrusions are provided at intervals in a direction in which the rib-shaped protrusion is continuously formed. Besides, the face of the other pressing member opposing the rib-shaped protrusion is formed flat. Thus, as shown in FIG. 4, in a compressed groove 15 formed on the surface sheet 14 and the absorbent body base material 12 after the groove embossing process, low compression sections 15a compressed at a low compression ratio and high compression sections 15b compressed at a higher compression ratio are alternately formed in the direction in which the compressed groove 15 extends.

Furthermore, a region in which this compressed groove 15 is formed has a higher rigidity. As shown in FIG. 4, substantial four compressed grooves are formed in the longitudinal direction on the base absorbent body 10, thus the base absorbent body 10 is hardly deformed in the width direction. For example, in a center region Rc in which holding sections 32 (described later) that protrude in the width direction are present, the base absorbent body 10 is brought into contact with a groin of the body and sandwiched thereby in the width direction. Thus, in a case where the rigidity in the width direction of the center region Rc is low, the base absorbent body 10 cannot resist the sandwiching by the groin and is folded along the center line CL. Accordingly, the top absorbent body 20 is sandwiched by the base absorbent body 10 from both sides, so that creases and the like formed in the longitudinal direction on the top absorbent body 20 makes it more difficult for the top absorbent body 20 to be in close contact with the groove of the buttocks. The compressed grooves 15 are formed selectively onto a region that needs the above mentioned rigidity.

The back face sheet 30 is, for example, a fluid-impermeable sheet made of a material such as polyethylene or polypropylene, and has a shape that is longer than the absorbent body base material 12 in the longitudinal direction and wider than the absorbent body base material 12 in the width direction. As shown in FIG. 6B, the absorbent body base material 12 adheres to the surface side of the back face sheet 30 with a hot-melt adhesive. Furthermore, the back face sheet 30 and the surface sheet 14 are joined by welding or the like at the front end section 10a and the rear end section 10b. Thus, the absorbent body base material 12 is held between the back face sheet 30 and the surface sheet 14.

As shown in FIG. 5, the back face side of the back face sheet 30 has "anti-displacement affixing sections 31" for adhesively fixing the sanitary napkin 1 to the inner face of the undergarment 90 in such a manner that after the sanitary napkin 1 is placed on the inner face of the undergarment 90, the sanitary napkin 1 is not displaced from that arranged position. The anti-displacement affixing sections 31 are, for example, a hot-melt adhesive applied to a predetermined area on the back face of the back face sheet 30, and continuously formed from the front end section 10a to the rear end section 10b of the base absorbent body 10.

Furthermore, as shown in FIG. 5, in order to strengthen the prevention of displacement between the undergarment 90 and the sanitary napkin 1, the holding sections 32 that protrude outward in the width direction are formed at both ends of the back face sheet 30 in the width direction. Also, the back face of the holding sections 32 has "anti-displacement affixing sections 33". The holding sections 32 are folded back outward, and adhesively fixed by the anti-displacement affixing sections 33 to the outer face of the undergarment 90. Note that the center position of the holding sections 32 in the longitudinal direction corresponds to the above-described point Z that is supposed to face the vaginal orifice.

As shown in FIG. 6B, the side sheets 40 are for forming the leakage-proof walls 46 in the vicinity of both end sections of the absorbent body base material 12 in the width direction. As shown in FIG. 4, the side sheets 40 are provided along the longitudinal direction, covering the surface sheet 14 from the surface side. Herein, the side sheets 40 are made of a hydrophobic sheet. Examples of the material thereof include a spunbond nonwoven fabric made of a synthetic resin fiber such as polypropylene or polyethylene.

More specifically, as shown in FIG. 4, a pair of the side sheets 40 in the width direction is symmetrically arranged relative to the center line CL with respect to the width direction. The side sheets 40 extend in the longitudinal direction from the front end section to the rear end section of the back face sheet 30, that is, to the external outline of the sanitary napkin 1. As shown in FIG. 6B, the side sheets 40 are respectively pressure-bonded and fixed to the surface sheet 14 in the vicinity of both end sections of the absorbent body base material 12 in the width direction, and thus fixed sections 44 are formed. The portions from the fixed sections 44 to end sections 46 function as free ends. Elastic members 48 are fixed to the end sections 46 along the longitudinal direction in a stretched state. Thus, in a case where the sanitary napkin 1 is curved in such a manner that the surface side is inside when the sanitary napkin 1 is worn, the elastic members 48 contract, so that the end sections 46 functioning as the free ends stand from the surface sheet 14 to become the leakage-proof walls 46. Herein, as shown in FIGS. 6A and 6C, the front end sections and the rear end sections in the longitudinal direction of the end sections 46 functioning as the leakage-proof walls are joined to the side sheets 40 with hot-melt adhesive in a state where the end sections 46 are laid down toward the surface sheet 14, and are non-standing sections that do not stand.

Furthermore, these side sheets 40 extend further outward in the width direction from their respective fixed sections 44. More specifically, their respective outer edges of the side sheets 40 reach outer edges of the back face sheet 30, that is, the outer edges of the sanitary napkin 1. The outer edges (see the hatched areas in FIG. 4) are joined by thermocompression bonding or the like to the outer edges of the back face sheet 30 in the width direction throughout the longitudinal direction. Note that, it is preferable that hot-melt adhesive HMA is interposed between layers of the sheets.

<Top Absorbent Body 20>

Figure 7:
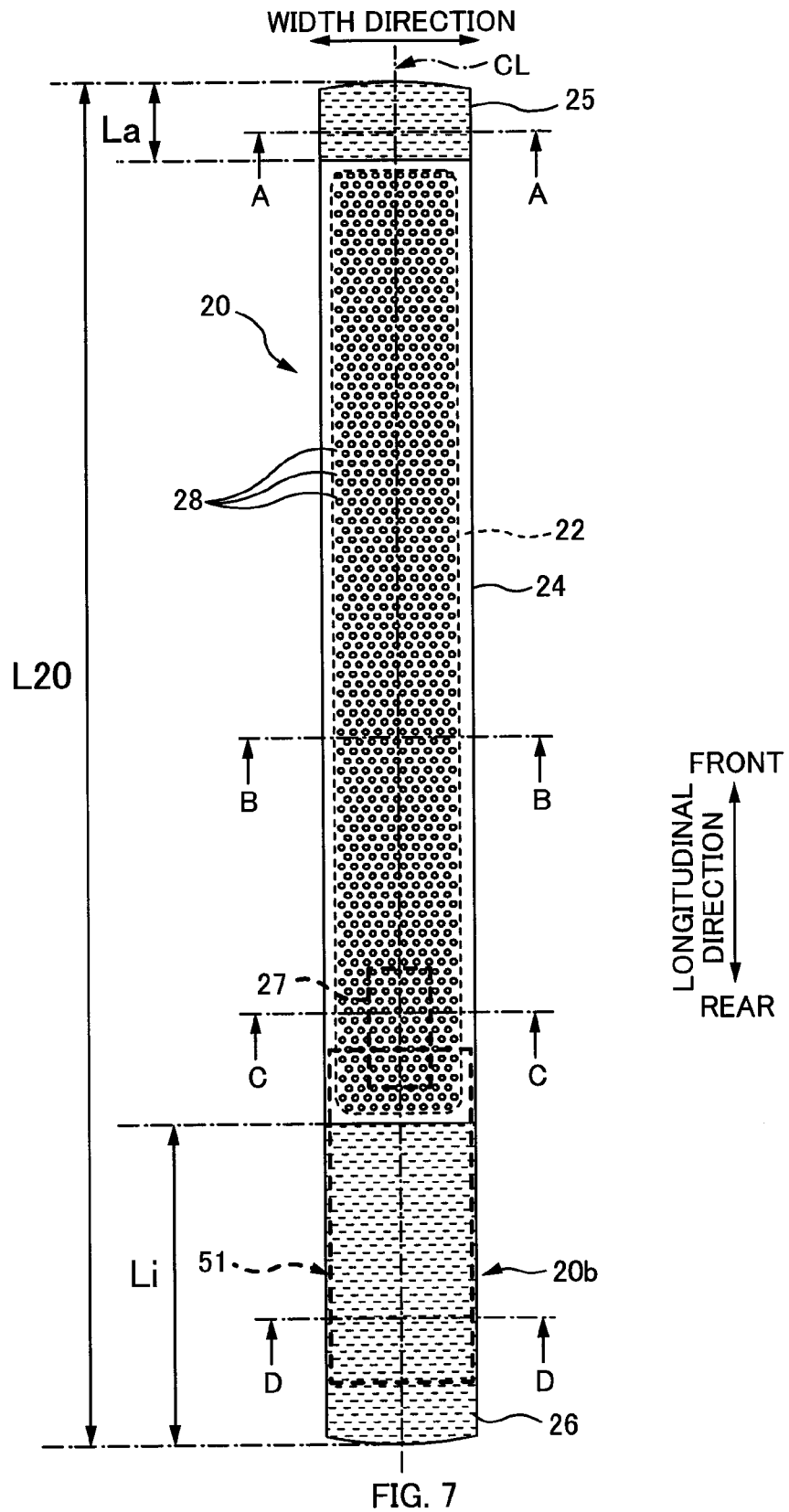
FIG. 7 is a plan view of a top absorbent body in an opened state.

FIG. 7 is a plan view of the top absorbent body 20 in an opened state. FIGS. 8A to 8D are cross-sectional views respectively taken along lines A-A, B-B, C-C, and D-D in FIG. 7.

The top absorbent body 20 has a pulverized pulp layered body 22 that absorbs fluid, an intermediate sheet 23 that is disposed closer to the surface side than the pulverized pulp layered body 22, and a shape retaining sheet 24 that wraps the pulverized pulp layered body 22 and the intermediate sheet 23 together and retains the pulverized pulp layered body 22 and the like in the shape of a long article that is elongated in the longitudinal direction.

The intermediate sheet 23 is a fluid-permeable sheet that has better fluid drawing properties than the shape retaining sheet 24. Examples of the material thereof include a through-air nonwoven fabric that is formed of a synthetic resin fiber such as polypropylene and the like. A perforation embossing process is performed on the intermediate sheet 23 and the shape retaining sheet 24 with overlapping, and thereby the intermediate sheet 23 is joined and integrated into the shape retaining sheet 24.

The perforation embossing process is performed using a pair of processing members (not shown) that oppose each other. More specifically, one of the processing members has conical protrusions, and another processing member opposing one has hole sections into which the protrusions are each inserted. The processing member on which the protrusions are formed is heated. Thus, when the conical protrusions form a large number of perforations 28 (see FIG. 1) by penetrating the intermediate sheet 23 and the shape retaining sheet 24 that overlap, the edges of the perforations are heat-sealed. Thereby, the intermediate sheet 23 is joined and integrated into the shape retaining sheet 24.

The shape retaining sheet 24 is a fluid-permeable sheet, and is made of, for example, the same material as that of the surface sheet 14 of the base absorbent body 10 described above. When viewed from above, the shape retaining sheet 24 that is opened flat as a sheet has a substantially rectangular. Then, in a state where a hot-melt adhesive is applied to the entire face of the shape retaining sheet 24 in an opened state, the shape retaining sheet 24 is rolled into a cylinder as shown in FIG. 8B, and both end sections 24e in the width direction are overlapped and joined with the hot-melt adhesive. In this state, the pulverized pulp layered body 22 and the intermediate sheet 23 are accommodated in the cylinder throughout the longitudinal direction.

Figure 8A:
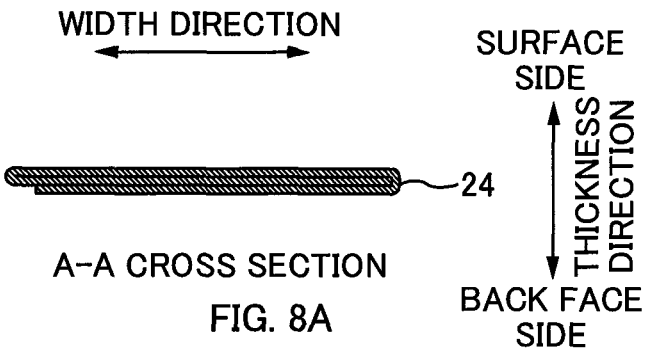
FIGS. 8A to 8D are cross-sectional views respectively taken along lines A-A, B-B, C-C, and D-D in FIG. 7.
Figure 8B:
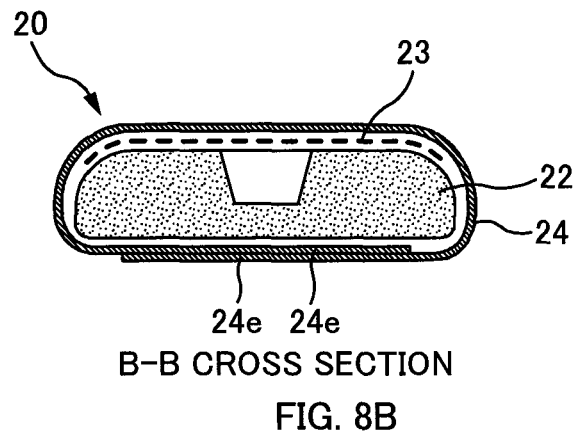
Figure 8C:
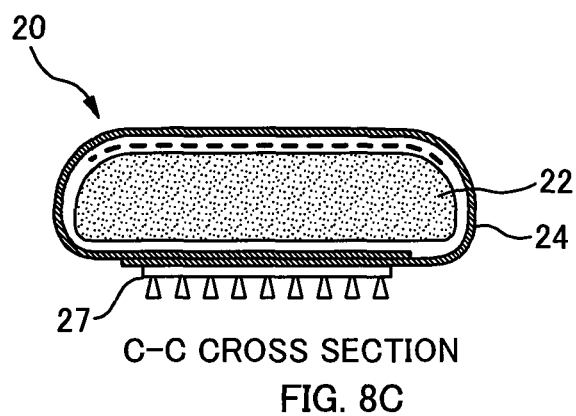
Figure 8D:
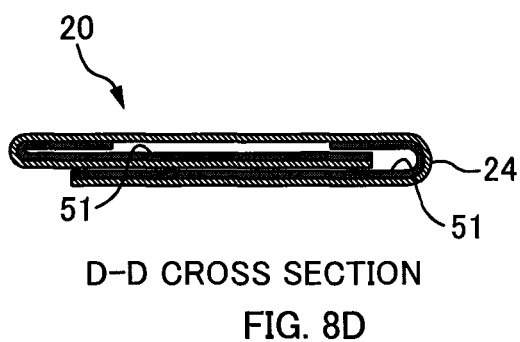

As shown in FIGS. 8A and 8D, the shape retaining sheet 24 is folded flat in a state where the front end section 20a and the rear end section 20b of the top absorbent body 20 do not contain the pulverized pulp layered body 22 or the intermediate sheet 23. Then, pressure-bonding by an embossing process is performed on the folded-flat portions with having a hot-melt adhesive (not shown) therebetween. Accordingly, the front end section 20a and the rear end section 20b of the shape retaining sheet 24 in the longitudinal direction (corresponding to a surface member) are sealed, and thus thin sealed sections 25 and 26 are formed. Herein, the length in the longitudinal direction of the front sealed section 25 is referred to as La, and the length in the longitudinal direction of the rear sealed section 26 is referred to as Li.

As shown in FIGS. 7 and 8C, the back face side of the top absorbent body 20 has a fastening section 27 for fixing the top absorbent body 20 to the surface of the base absorbent body 10. With the fastening section 27, the top absorbent body 20 can be maintained at a preferable position that is adjusted when wearing the sanitary napkin 1. Moreover, also in a production process, the top absorbent body 20 is fixed to the base absorbent body 10 by the fastening section 27, and thus relative movement between the top absorbent body 20 and the base absorbent body 10 is restricted.

As the fastening section 27, an adhesive member, a hook member (a male member of a hook-and-loop fastener), or the like can be used. Examples of the hook member, in which a plurality of needle-like pins inclined at a predetermined angle from a plane are arranged, include a hook member in which the hook member is hardly hooked on a fiber when being pulled in one direction and is easily released in this direction, and the hook member is easily hooked on a fiber when being pulled in another direction and is easily fastened in this direction. Furthermore, in order to make it easier to fasten, a female member of the hook-and-loop fastener corresponding to the male member of the hook-and-loop fastener that is provided on the side of the top absorbent body 20 may be provided on the side of the base absorbent body 10.

As shown in FIGS. 7 and 8D, leakage-proof sheets 51 are arranged inside the shape retaining sheet 24, from the sealed section 26 to the fastening section 27 (described later) on the rear end side of the top absorbent body 20. The leakage-proof sheets 51 are fluid-impermeable sheets. For example, in a case where the top absorbent body 20 is folded in such a manner that the portion in which the pulverized pulp layered body 22 is present is on the surface side and the sealed section 26 is on the back face side, by the amount by which the user pulls up the top absorbent body 20 rearward when wearing the sanitary napkin 1, and the folded portion protrudes rearward from the rear end edge of the base absorbent body 10, the leakage-proof sheets 51 arranged in the sealed section 26 on the back face side of the folded portion can prevent fluid that has been absorbed by the pulverized pulp layered body 22 on the surface side of the folded portion from seeping out to the undergarment 90. Furthermore, as shown in FIG. 8D, the leakage-proof sheets 51 are not arranged on the surface side, so that fluid absorption of the portion in which the pulverized pulp layered body 22 of the top absorbent body 20 is present is not inhibited. Herein, as a material of the leakage-proof sheets 51, for example, a non-perforated film that can completely block fluid and is made of polyethylene or polypropylene is desirable. However, materials that cannot completely block fluid also may be used. Examples thereof include a nonwoven fabric made of a water-repellent fiber.

<Joining of Top Absorbent Body 20 and Base Absorbent Body 10>

In a state where the top absorbent body 20 is overlaid on the surface side of the base absorbent body 10 with their center lines CL with respect to the width direction being aligned as shown in FIG. 1, the front end section 20a of the top absorbent body 20 and the front end section 10a of the base absorbent body 10 are permanently joined, and the rear end section 20b of the top absorbent body 20 and the rear end section 10b of the base absorbent body are permanently joined. The portion on the front end side subjected to the permanent joining is referred to as a first joined section 10g, and the portion on the rear end side subjected to the permanent joining is referred to as a second joined section 10h. These joined sections are indicated as darkened areas in FIG. 4. In the present embodiment, permanent joining is performed by applying a hot-melt adhesive (indicated by HMA in FIG. 4) to the first joined section 10g and the second joined section 10h of the base absorbent body 10, and letting the portions to which the adhesive has been applied adhere to the front end section 20a and the rear end section 20b of the top absorbent body 20.

Here, the permanent joining refers to an inseparable state in which the top absorbent body 20 and the base absorbent body 10 have been joined firmly to an extent that damage inevitably occurs to at least either one the top absorbent body 20 or the base absorbent body 10 when the top absorbent body 20 and the base absorbent body 10 are pulled apart with the intention of separating them. The method for this permanent joining is not limited to the method using a hot-melt adhesive, and the permanent joining may be performed using a groove embossing process or the like.

As shown in FIG. 2, the first joined section 10g on the front end side extends through the sealed section 25 (longitudinal length La) of the top absorbent body 20 and further into the portion in which the pulverized pulp layered body 22 is present (longitudinal length Lg). If the top absorbent body 20 is permanently joined only at the sealed section 25, the rigidity becomes too low, and thus, as a whole, the top absorbent body 20 is easily displaced loosely in the front-rear direction.

In the sanitary napkin 1 of the present embodiment, the length L20 (FIG. 7) in the longitudinal direction of the center line CL of the top absorbent body 20 is equal to the length L10 (FIG. 4) in the longitudinal direction of the center line CL of the base absorbent body 10 (L20=L10). Furthermore, the top absorbent body 20 and the base absorbent body 10 are permanently joined at the first joined section 10g and the second joined section 10h in a state where substantially the entire back face of the top absorbent body 20 is in contact with the surface of the base absorbent body 10, the top absorbent body 20 does not protrude in the longitudinal direction from the base absorbent body 10, the front end of the top absorbent body 20 and the front end of the base absorbent body 10 are aligned with each other, and the rear end of the top absorbent body 20 and the rear end of the base absorbent body 10 are aligned with each other.

When the length in the longitudinal direction of the first joined section 10g is taken as Lg, and the length in the longitudinal direction of the second joined section 10h is taken as Lh (FIG. 4), an absorbent body length L, which is the length of the center line CL on the back face side of the top absorbent body 20 between the first joined section 10g and the second joined section 10h, is L=L20−Lg−Lh, and a main body section length M, which is the length of the center line CL on the surface side of the base absorbent body 10 between the first joined section 10g and the second joined section 10h, is M=L10−Lg−Lh. More specifically, the absorbent body length L is equal to the main body section length M.

Herein, the absorbent body length L and the main body section length M are lengths in a natural state in which no force is applied from the outside to the sanitary napkin 1. Furthermore, the absorbent body length L is the length along the back face side on which the top absorbent body 20 opposes the base absorbent body 10, and the main body section length M is the length along the surface side on which the base absorbent body 10 opposes the top absorbent body 20. Thus, the back face of the top absorbent body 20 is in contact with the base absorbent body 10 in a natural state.

Then, since the absorbent body length L is equal to the main body section length M (FIG. 4), in a process of permanently joining the top absorbent body 20 and the base absorbent body 10, the joining can be performed in a state where the top absorbent body 20 and the base absorbent body 10 are opened flat. Thus, production process becomes easy. The reason for this is that if the absorbent body length L is longer than the main body section length M, in the permanent joining process, the top absorbent body 20 has to be folded flat or to be lifted from the base absorbent body 10 by the amount by which the absorbent body length L is longer than the main body section length M.

Furthermore, since the absorbent body length L is equal to the main body section length M in the sanitary napkin 1 in a natural state, the sanitary napkin 1 in a natural state is flat with respect to the horizontal direction (in a strict sense, since the sanitary napkin 1 has a thickness in the thickness direction, the back face of the base absorbent body 10 becomes flat). Herein, the sanitary napkin 1 of the present embodiment has the elastic members 48 that are stretched in the longitudinal direction so that the side sheets 40 are erected to become the leakage-proof wails 46. Thus, actually, the base absorbent body 10 in a natural state is slightly curved with respect to the horizontal direction in such a manner that the surface side of the base absorbent body 10 is on the inner side. However, in the present embodiment, this state is expressed as that the sanitary napkin 1 in a natural state is substantially flat with respect to the horizontal direction. Furthermore, the rigidity of the rear sealed section 26 of the top absorbent body is lower than that of other portions in the top absorbent body 20 having the pulverized pulp layered body 22. Thus, even if the base absorbent body 10 is slightly curved, the sealed section 26 deforms its shape according to the curve of the base absorbent body 10. Accordingly, the state is kept in which the back face of the top absorbent body 20 and the surface of the base absorbent body 10 are in contact with each other.

<Wrapping>

FIGS. 9A to 9D are explanatory views of the manner in which the sanitary napkin 1 is wrapped. The sanitary napkin 1 is folded flat in four parts, by being folded at three positions P1, P2, and P3 in the longitudinal direction together with a rectangle wrapping sheet 36 disposed on the back face side of the sanitary napkin 1. Finally, as shown in FIG. 9D, the wrapping sheet 36 is fixed by tape 38, and becomes like a pouch with outer end edges 36c along the longitudinal direction being adhesively sealed. In this manner, the sanitary napkin 1 is in a wrapped state.

Herein, at the time of wrapping, the sanitary napkin 1 is folded flat in such a manner that the top absorbent body 20 is inner side in a state where the entire back face of the top absorbent body 20 is in contact with the surface of the base absorbent body 10. Thus, the entire back face of the top absorbent body 20 is in contact with the surface of the base absorbent body 10, in a natural state where the sanitary napkin 1 has been unwrapped.

As shown in FIG. 9A, the holding sections 32 on both sides of the sanitary napkin 1 are folded back toward the top absorbent body. Note that protection sheets 35 adhere to the holding sections 32 in such a manner that the face of the protection sheets 35 to which adhesives 33 and a release agent have been applied and the back face of the holding sections 32 before being folded back oppose each other. Next, the holding sections 32 to which the protection sheets 35 have adhered are folded back toward the top absorbent body 20, and the two protection sheets 35 are integrally linked to each other, at the portion in which the protection sheets 35 overlap in the middle in the width direction, by an adhesive that has been applied in advance. Then, only an adhesive is applied to the face of the integrally linked protection sheets 35 opposite to the face to which the release agent has been applied. The adhesive on the protection sheets 35 and the rear end section of the wrapping sheet 36 overlap when the sanitary napkin 1 is folded flat. Accordingly, when the user unwraps the sanitary napkin 1, the adhesives 33 are transferred due to the action of the release agent and remain on the holding sections 32, and thus the "anti-displacement affixing sections 33" are formed on the holding sections 32.

<Fitting the Sanitary Napkin 1 on the Body>

Regarding the sanitary napkin 1 that has been handed over to the user in the above-described wrapped state, the user opens the seal of the wrapping sheet 36 by peeling away the tape 38, and thus the protection sheets 34 and 35 are peeled away, and the anti-displacement affixing sections 31 on the back face of the back face sheet 30 and the anti-displacement affixing sections 33 on the back face of the holding sections 32 are exposed. The unwrapped sanitary napkin 1 is, first, adhesively fixed to the undergarment 90.

Figure 10:
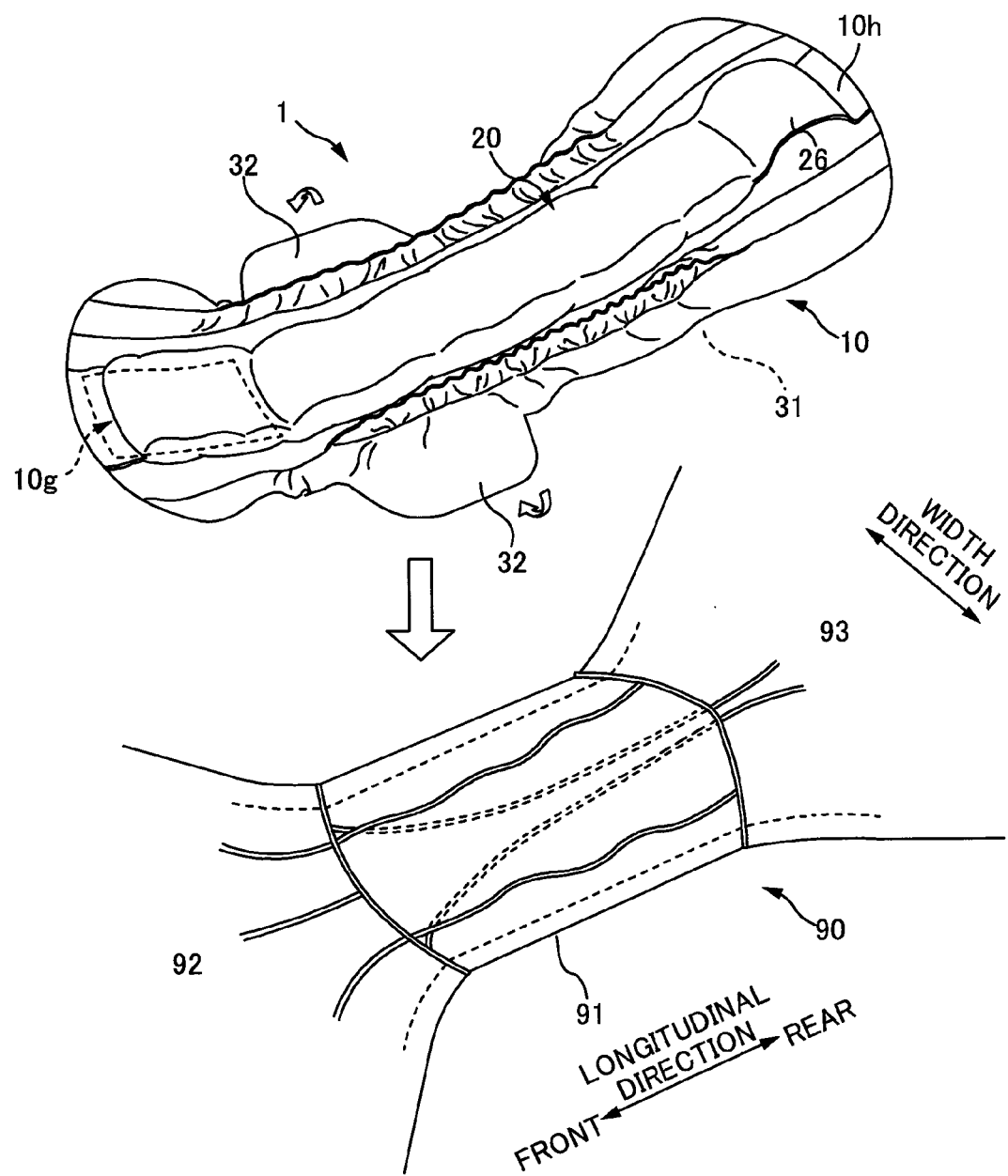
FIG. 10 is a view showing the manner in which the sanitary napkin is attached to the inner face of an undergarment.
Figure 11:
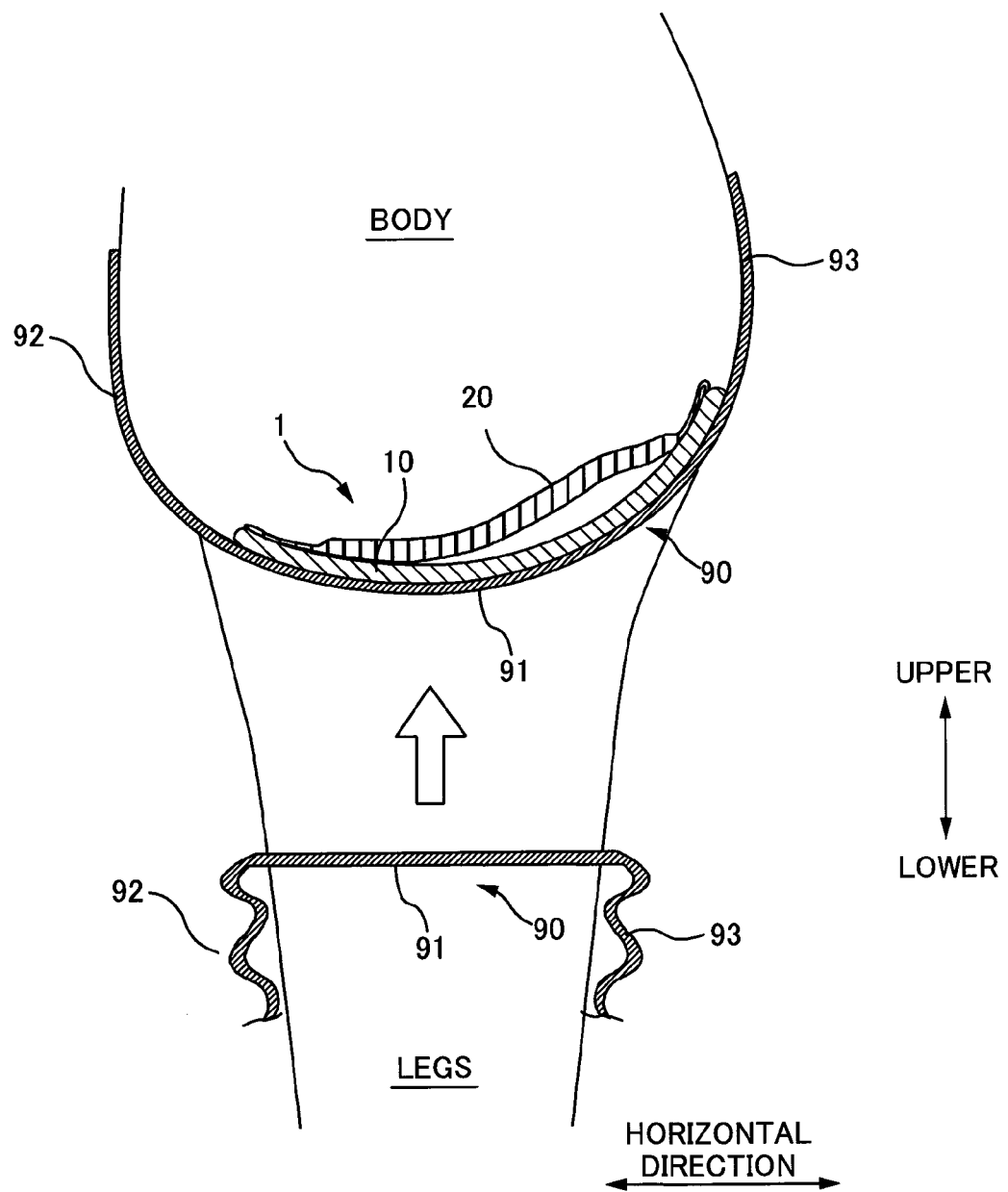
FIG. 11 is a view showing a state in which the undergarment has been pulled down from the body and a state in which the undergarment is in close contact with the body.

FIG. 10 is a view showing the manner in which the sanitary napkin 1 is attached to the inner face of the undergarment 90. FIG. 11 is a view showing a state in which the undergarment 90 has been pulled down from the body and a state in which the undergarment 90 fits closely to the body. In a state where the undergarment 90 fits closely to the body, it is impossible to wear the sanitary napkin 1. Thus, the user moves the undergarment away from the body, for example, by pulling down the undergarment 90 from the body. Next, the user places the sanitary napkin 1 in such a manner that the front side of the sanitary napkin 1 is positioned on the side of a front body 92 of the undergarment 90, the rear side of the sanitary napkin 1 is positioned on the side of a back body 93 of the undergarment 90, and the center region Rc (the holding sections 32) of the sanitary napkin 1 is positioned at a crotch section (the section under the groin) 91 of the undergarment 90, and then the anti-displacement affixing sections 31 on the back face of the sanitary napkin 1 are adhesively fixed to the inner face of the undergarment 90. Then, the user folds back the holding sections 32 outward, and adhesively fixes the holding sections 32 to the outer face of the undergarment 90 using the anti-displacement affixing sections 33.

Here, in a state where the undergarment 90 fits closely to the body as shown in FIG. 11, the undergarment 90 is curved with respect to the horizontal direction, but in a state where the undergarment 90 is pulled down from the body, the crotch section 91 and the vicinity of the crotch section 91 of the undergarment 90 become substantially flat with respect to the horizontal direction. Furthermore, as described above, the sanitary napkin 1 is also substantially flat with respect to the horizontal direction in a natural state where the sanitary napkin 1 has been unwrapped. More specifically, the back face of the sanitary napkin 1 that is flat with respect to the horizontal direction is caused to adhere to the inner face of the undergarment 90 (the crotch section 91 and its vicinity) that is flat with respect to the horizontal direction, so that a relatively large adhesion area can be obtained. That is to say, obtaining a large adhesion area means adhesively fixing the sanitary napkin 1 securely to the undergarment 90. Not only in a case where the undergarment 90 has been pulled down from the body as shown in FIG. 11, but also in a case where the undergarment 90 has been completely removed from the body, the crotch section 91 of the undergarment 90 can be made flat with respect to the horizontal direction, and the sanitary napkin 1 is adhesively fixed securely to the undergarment 90.

Hereinafter, a sanitary napkin 2 that is different from the sanitary napkin 1 of the present embodiment will be described as a comparative example. FIG. 12 is a schematic view of cross sections of the sanitary napkin 1 of the present embodiment and the sanitary napkin 2 of the comparative example. In the sanitary napkin 1 of the present embodiment, the absorbent body length L, which is the length on the back face of the top absorbent body 20 from the first joined section 10g to the second joined section 10h, is equal to the main body section length M, which is the length on the surface of the base absorbent body 10 from the first joined section 10g to the second joined section 10h. Conversely, in the sanitary napkin 2 of the comparative example, an absorbent body length L', which is the length on the back face of a top absorbent body 20' from the first joined section 10g to the second joined section 10h, is shorter than a main body section length M', which is the length on the surface of a base absorbent body 10 from the first joined section 10g to the second joined section 10h.

In a case where the absorbent body length L' is shorter than the main body section length M', in a natural state, the top absorbent body 20' is positioned above the base absorbent body 10', and the base absorbent body 10' is curved with respect to the horizontal direction as shown in FIG. 12. More specifically, as in the sanitary napkin 2 of the comparative example, in a case where the back face of the base absorbent body 10' that is curved with respect to the horizontal direction is adhesively fixed to the inner face of the undergarment 90 (the crotch section 91 and its vicinity) that is substantially flat with respect to the horizontal direction, the area in which the back face of the base absorbent body 10' adheres to the inner face of the undergarment 90 is smaller than that in the sanitary napkin 1 of the present embodiment. More specifically, the sanitary napkin 2 of the comparative example is not adhesively fixed securely to the undergarment 90, and the sanitary napkin 2 is displaced loosely, for example, when the user pulls up the undergarment 90. Accordingly, it is difficult to bring the sanitary napkin 2 of the comparative example into contact with the body.

Furthermore, in a case where the top absorbent body 20' of the sanitary napkin 2 of the comparative example in FIG. 12 has a stretchable member, the base absorbent body 10' can be made flat or nearly flat with respect to the horizontal direction by stretching the sanitary napkin 2 by application of an external force. However, the user has to adhesively fix the sanitary napkin 2 to the inner face of the undergarment 90 while stretching the sanitary napkin 2 with her hand. Thus, it is not easy for the user to adhesively fix the sanitary napkin 2 of the comparative example to the undergarment 90. Moreover, the adhesive strength of the anti-displacement affixing sections 31 on the back face of the sanitary napkin 2 is to the extent that the user can easily peel away the sanitary napkin from the undergarment 90. Thus, even if the user adhesively fixes the sanitary napkin 2 to the undergarment 90 while stretching the sanitary napkin 2 so as to increase the area in which the back face of the base absorbent body 10 adheres to the inner face of the undergarment 90, the adhesive strength of the anti-displacement affixing sections 31 may be removed due to the contraction force of the top absorbent body 20'. As a result, the sanitary napkin 2 of the comparative example cannot be adhesively fixed securely to the undergarment 90. Thus, when the undergarment 90 is pulled up, the sanitary napkin 2 is displaced loosely.

In addition to the above, in the sanitary napkin 1 of the present embodiment, Substantially the entire back face of the top absorbent body 20 is in contact with the base absorbent body 10, in a natural state where the sanitary napkin 1 has been unwrapped. Thus, the user can press the top absorbent body 20 from above (from the surface side) with her hand when causing the anti-displacement affixing sections 31 of the base absorbent body 10 to adhere to the inner face of the undergarment 90. However, in the sanitary napkin 2 of the comparative example, the top absorbent body 20' is positioned above the base absorbent body 10' with a space A interposed therebetween. Thus, the user has to insert her hand into the space A between the top absorbent body 20' and the base absorbent body 10' to cause the anti-displacement affixing sections 31 of the base absorbent body 10' to adhere to the inner face of the undergarment 90. Thus, it is not easy for the user to adhesively fix the sanitary napkin 2 of the comparative example to the undergarment 90.

Furthermore, in the sanitary napkin 1 of the present embodiment, the top absorbent body 20 and the base absorbent body 10 are joined in such a manner that their middle sections in the width direction are matched, and the sanitary napkin 1 comes into contact with the body in a state where substantially the entire back face of the top absorbent body 20 is in contact with the base absorbent body 10. Thus, the top absorbent body 20 can reliably come into contact with the groove section of the body without displacement of the top absorbent body 20 to the left or right, when the undergarment 90 is pulled up.

In summary, the sanitary napkin 1 of the present embodiment is characterized in that the absorbent body length (=L), which is the length of the top absorbent body 20 between the first joined section and the second joined section, is equal to or longer than the main body section length (=M), which is the length of the base absorbent body 10 between the first joined section and the second joined section.

Accordingly, in a natural state, the base absorbent body 10 is not curved downward with respect to the top absorbent body 20, and thus the sanitary napkin 1 can be kept substantially flat with respect to the horizontal direction. Thus, the back face of the base absorbent body 10 can be adhesively fixed securely to the inner face of the undergarment 90. As a result, loose displacement of the sanitary napkin 1 can be suppressed when the undergarment 90 to which the sanitary napkin 1 has been adhesively fixed is made to fit closely to the body. Thus, the user can easily bring the sanitary napkin 1 into contact with the body. Furthermore, in the sanitary napkin 1 of the present embodiment, in a natural state, the top absorbent body 20 is not lifted above the base absorbent body 10, and the back face of the top absorbent body 20 is in contact with the surface of the base absorbent body 10. Thus, it is easy to adhesively fix the anti-displacement affixing sections 31 of the base absorbent body 10 to the inner face of the undergarment 90. That is to say, the sanitary napkin 1 of the present embodiment is a sanitary napkin that can be easily worn.

In this manner, the anti-displacement affixing sections 31 on the back face of the sanitary napkin 1 of the present embodiment are caused to adhere to the inner face of the undergarment 90, the anti-displacement affixing sections 33 on the back face of the holding sections 32 are caused to adhere to the outer face of the undergarment 90, the sanitary napkin 1 is adhesively fixed securely to the undergarment 90, and then the undergarment 90 is pulled up together with the sanitary napkin 1 toward the body.

Figure 13:
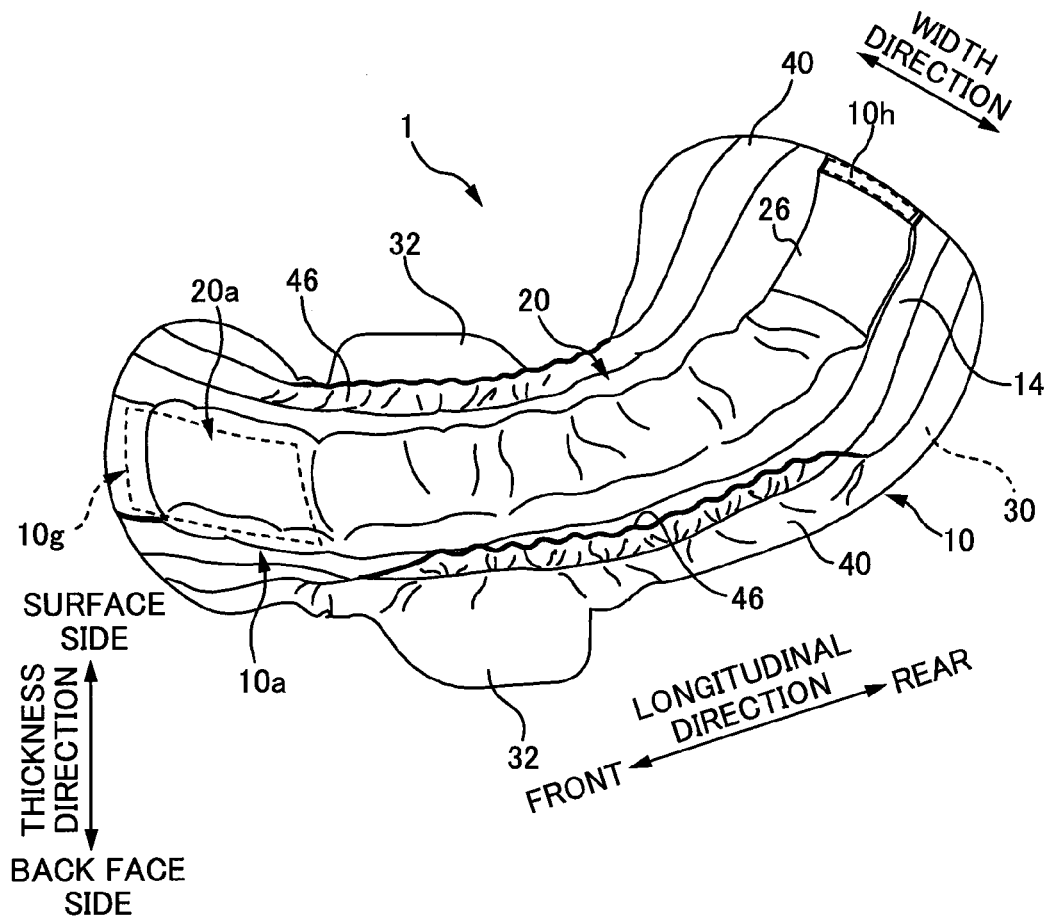
FIG. 13 is a view showing the manner in which the sanitary napkin has been come into contact with the body in a state where the back face of the top absorbent body is in contact with the base absorbent body.

FIG. 13 is a view showing the manner in which the sanitary napkin 1 has been brought into contact with the body in a state where the back face of the top absorbent body 20 is in contact with the base absorbent body 10. The sanitary napkin 1 of the present embodiment has a thickness in the thickness direction, and the absorbent body length L is equal to the main body section length M. Thus, when the sanitary napkin 1 is curved fitting closely to the body in a state where the entire back face of the top absorbent body 20 is in contact with the base absorbent body 10, a large number of creases as shown in FIG. 13 are irregularly formed on the top absorbent body 20 on the inner side. More specifically, in a case where the sanitary napkin 1 is brought into contact with the body simply by pulling up the undergarment 90 to which the sanitary napkin 1 is attached, a gap is formed between the surface sheet 14 and the pulverized pulp layered body 22 due to the large number of creases formed on the top absorbent body 20, and fluid may leak from the gap.

However, in the sanitary napkin 1 of the present embodiment, the top absorbent body 20 and the base absorbent body 10 are separable from each other between the first joined section 10g and the second joined section 10h, and thus the user detaches the temporary joined section formed by the fastening section 27 between the top absorbent body 20 and the base absorbent body 10, and pulls up the top absorbent body 20 rearward so that the top absorbent body 20 fits closely to the groove of the body. Accordingly, the creases on the top absorbent body 20 shown in FIG. 13 are eliminated, and the top absorbent body 20 is placed in the groove of the body and fits closely thereto. Thus, leakage of fluid can be prevented.

Figure 14:
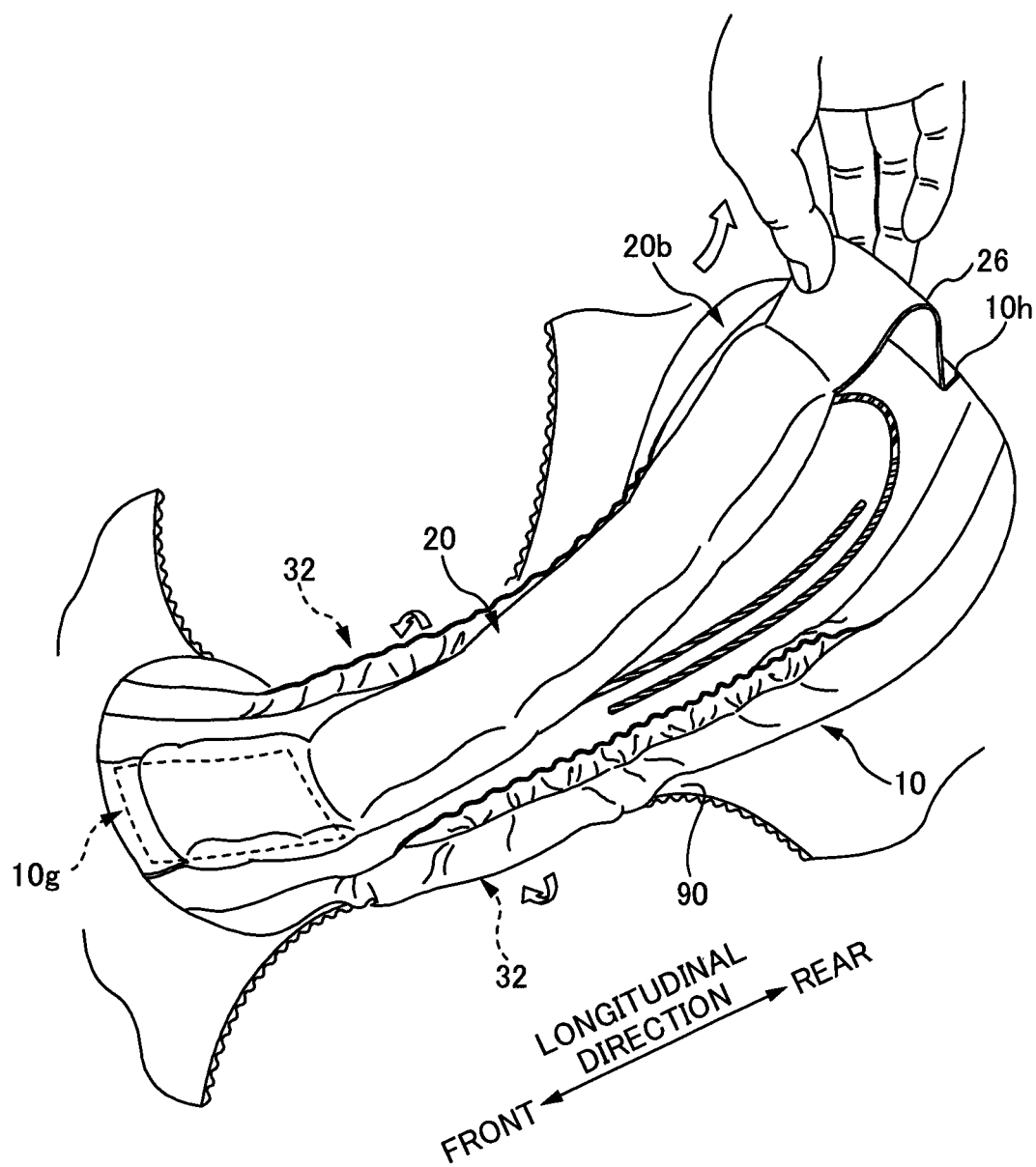
FIG. 14 is a view showing the manner in which the user pulls up the top absorbent body.
Figure 15A:
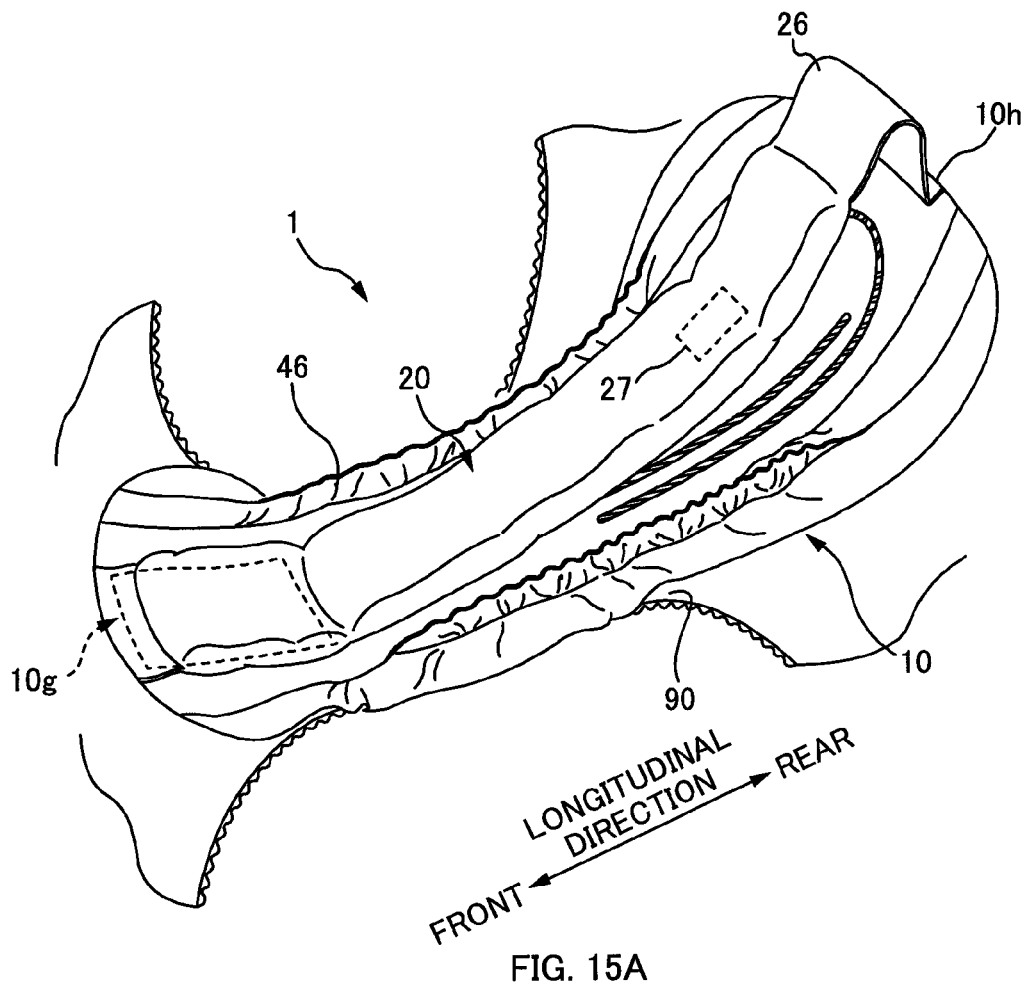
FIG. 15A is a view showing the manner in which an adjusted position of the top absorbent body is maintained.

FIG. 14 is a view showing the manner in which the user pulls up the top absorbent body 20. FIG. 15A is a view showing the manner in which an adjusted position of the top absorbent body 20 is maintained. The user can adjust the top absorbent body 20 so that it fits closely to the groove of the body by picking up the rear sealed section 26 of the top absorbent body 20 and pulling up the top absorbent body 20. That is to say, the sealed section 26 functions as a pick-up section. Then, the user fixes the top absorbent body 20 to the base absorbent body 10 using the fastening section 27, at the preferable position of the top absorbent body 20 obtained by the adjustment, thereby preventing the top absorbent body 20 from being displaced from the preferable position. In this manner, the sanitary napkin 1 is completely worn.

Figure 15B:
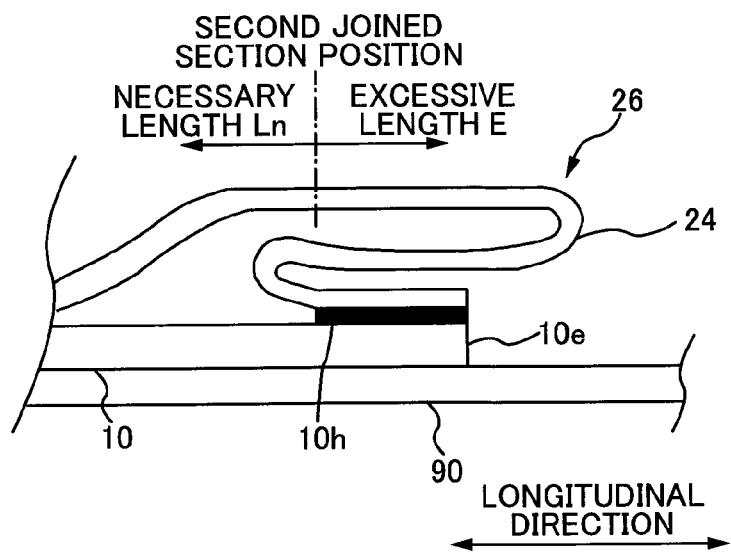
FIG. 15B is a view showing the rear end of the sanitary napkin that has been completely worn.

The top absorbent body 20 is pulled up toward the second joined section 10h on the rear side so that the top absorbent body 20 fits to groove of the body. Here, since the top absorbent body 20 is permanently joined to the base absorbent body 10 at the second joined section 10h, the sanitary napkin 1 is worn with an excessive portion (an excessive length E) of the top absorbent body 20 formed when the top absorbent body is pulled up rearward being folded. FIG. 15B is a cross-sectional view showing the rear end section of the sanitary napkin 1 that has been completely worn (enlarged view of the rear end section in FIG. 15A). Herein, the position of the front end of the second joined section 10h in the longitudinal direction is referred to as a second joined section position. Further, the excessive portion of the top absorbent body 20 refers to a portion of the top absorbent body 20 not fitting closely to the groove of the body. The excessive length E is the length of the excessive portion, and refers to the length obtained by subtracting a necessary length Ln, which is the length of the top absorbent body 20 from the first joined section 10g to the second joined section position (FIG. 15B) in a state where the top absorbent body 20 fits closely to the groove of the body as shown in FIG. 15A, from the absorbent body length L (the length of the top absorbent body 20 from the first joined section 10g to the second joined section 10h in a natural state) (E=L−Ln).

Since the top absorbent body 20 is pulled up rearward, the rear portion in the top absorbent body 20 is folded as the excessive portion. The rear end side of the top absorbent body 20 is the sealed section 26 that does not have the pulverized pulp layered body 22, and thus its rigidity is lower than that of other portions in the top absorbent body 20 having the pulverized pulp layered body 22. More specifically, the sealed section 26 having low rigidity is folded as the excessive portion. Herein, since the rigidity of the sealed section 26 is low, even if the user does not fold the excessive portion of the top absorbent body 20, the sealed section 26 is folded on itself when the top absorbent body 20 is pulled up rearward. Furthermore, since the sealed section 26 is thin in the thickness direction, when the sealed section 26 is folded as the excessive portion, the folded portion of the top absorbent body 20 can be prevented from being too thick in the thickness direction.

If the pulverized pulp layered body 22 is present up to the rear end section of the top absorbent body 20, the rigidity of the portion of the top absorbent body 20, when folded as the excessive length E, becomes high. Thus, it is difficult to fold the excessive portion of the top absorbent body 20, and it is difficult for the user to adjust the position of the top absorbent body 20. Furthermore, if the portion of the top absorbent body 20 in which the pulverized pulp layered body 22 is present and that is thick in the thickness direction is folded, the folded portion becomes too thick in the thickness direction. As a result, a gap is formed in the thickness direction between the folded portion and the other portion, and the user has a foreign-body sensation when wearing sanitary napkin 1.

Herein, the top absorbent body 20 is pulled up rearward in order to make the top absorbent body 20 fit closely to the groove of the body and to eliminate the large number of creases formed on the top absorbent body 20 as shown in FIG. 13. Then, the preferable position of the top absorbent body 20 is maintained by the fastening section 27, and thus the top absorbent body 20 is stretched along the groove of the body at least from the first joined section 10g to the fastening section 27. Thus, the sealed section 26 is positioned closer to the rear side than the fastening section 27 as in the sanitary napkin 1 of the present embodiment. More specifically, the fastening section 27 is disposed between the first joined section 10g and the sealed section 26, and thus the sealed section 26 is folded as the excessive portion of the top absorbent body 20.

Moreover, the configuration was described in which the leakage-proof sheets 51 are arranged inside the shape retaining sheet 24 of the sealed section 26 (FIG. 8D), but there is no limitation to this. In a case where the sealed section 26 is folded as the excessive length E as in FIG. 15B, the folded sealed section 26 may protrude rearward from a rear end edge 10e of the sanitary napkin, and the surface side of the shape retaining sheet 24 may oppose the undergarment 90. At that time, if fluid excreted from the bodily discharge opening flows along the surface side of the shape retaining sheet 24 to reach the surface side of the shape retaining sheet 24 of the sealed section 26, the undergarment 90 gets dirty. Thus, for example, the surface side of the shape retaining sheet 24 of the sealed section 26 may further include a fluid-impermeable sheet, or the sealed section 26 may be constituted not by the shape retaining sheet 24 but by a fluid-impermeable sheet.

FIRST MODIFIED EXAMPLE

In the sanitary napkin 1 described above, the absorbent body length L is equal to the main body section length M, but there is no limitation to this. As long as the absorbent body length L is equal to or longer than the main body section length M in the sanitary napkin, the base absorbent body 10 can be kept substantially flat with respect to the horizontal direction, and thus the user can easily wear the sanitary napkin. For example, the absorbent body length L may be longer than the main body section length M. In this case, the user can easily adjust the position of the top absorbent body 20.

However, if the absorbent body length L is too long with respect to the main body section length M, the excessive length E increases, and thus much more effort is required to handle the excessive length E when pulling up the top absorbent body 20 rearward and fixing the position of the top absorbent body 20.

Furthermore, in the production process of joining both ends of the top absorbent body 20 and the base absorbent body 10, for example, the top absorbent body 20 has to be folded flat or to be lifted from the base absorbent body 10 by the amount by which the absorbent body length L is longer than the main body section length M. Thus, the joining process becomes complicated compared with the case in which the absorbent body length L is equal to the main body section length M.

SECOND MODIFIED EXAMPLE

Figure 16:
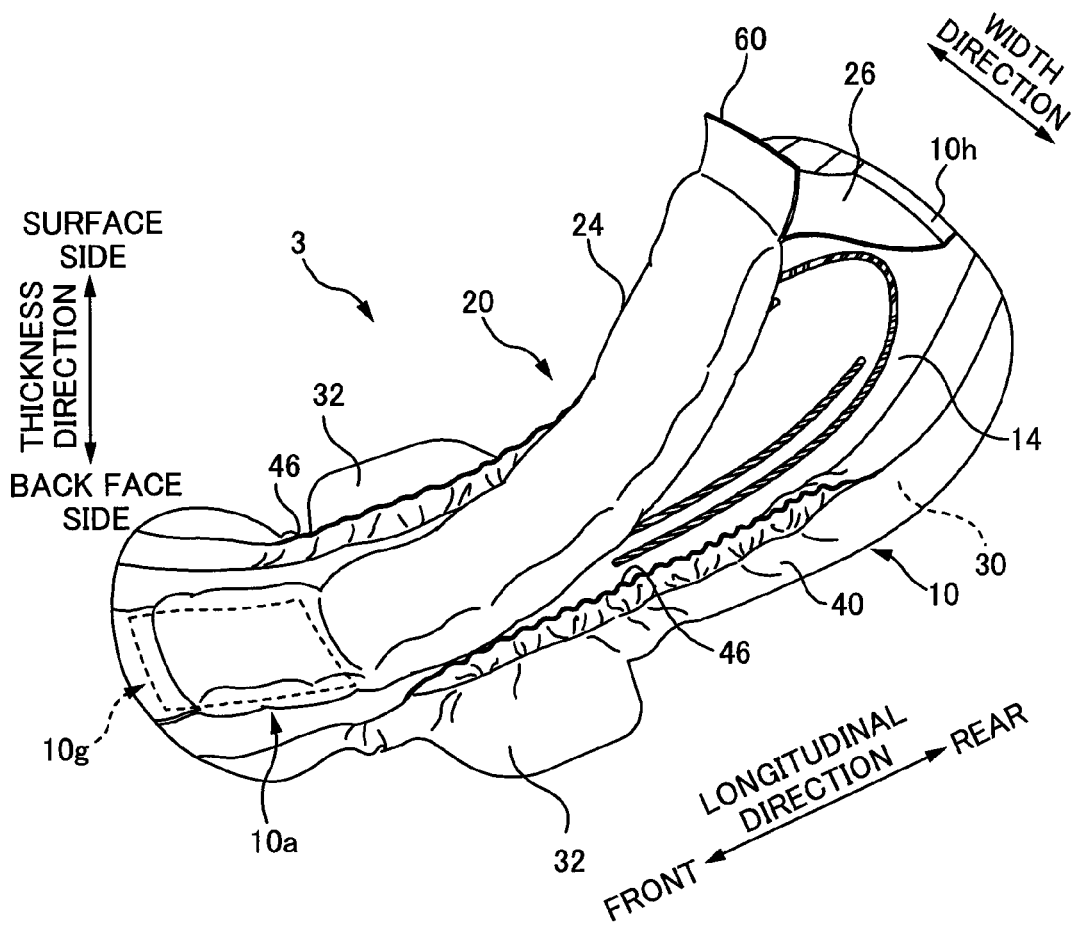
FIG. 16 is a view showing a sanitary napkin that is a modified example of the sanitary napkin of the present embodiment.

FIG. 16 is a view showing a sanitary napkin 3 that is a modified example of the sanitary napkin 1 of the present embodiment. The sanitary napkin 3 of the second modified example is provided with a pick-up section 60 that the user can pick up when pulling up the top absorbent body 20 for close fitting to the groove of the body. In a case where both ends of the top absorbent body 20 and the base absorbent body 10 are permanently joined, if the pick-up section 60 is provided, the user can easily pull up the top absorbent body rearward.

Furthermore, if the pick-up section 60 is not included in the absorbent body length L (the length of the top absorbent body 20 from the first joined section 10g to the second joined section 10h), and the absorbent body length L is equal to or longer than the main body section length M, the sanitary napkin 3 can be made substantially flat with respect to the horizontal direction. More specifically, the user can easily wear the sanitary napkin 3.

Herein, the pick-up section 60 may be attached later, or both ends of the top absorbent body 20 and the base absorbent body 10 may be joined after the shape retaining sheet is folded, the length of the portion that does not have the pulverized pulp layered body 22 is set to a length that enables both the sealed section 26 and the pick-up section 60 to be formed, and then the pick-up section 60 is formed.

Other Embodiments

In the foregoing embodiment, both end sections of the top absorbent body 20 and the base absorbent body 10 were permanently joined, but there is no limitation to this. For example, either one of the ends of the top absorbent body 20 may be temporarily joined to the base absorbent body 10 to an extent that the user can easily separate this end. However, in a case where only the front end section is permanently joined, when the user of the sanitary napkin pulls down the undergarment, with respect to the base absorbent body 10 that moves downward together with the undergarment 90, the top absorbent body 20 sandwiched by the groove is gradually pulled downward and finally removed from the groove. Thus, at that time, the top absorbent body 20 may topple forward using the permanent joined section as a fulcrum. In this case, the top absorbent body 20 that has absorbed menstrual blood and the like is brought into contact with the front body or its vicinity of the undergarment, and the undergarment may get dirty. More specifically, if both end sections are permanently joined, the undergarment can be prevented from getting dirty.

In the foregoing embodiment, the preferable position of the top absorbent body 20 when worn was maintained using the fastening section 27, but there is no limitation to this. The fastening section 27 may be not provided. In this case, the position of the top absorbent body 20 may be fixed by setting the top absorbent body 20 to be close contact with the groove section of the body and be sandwiched thereby.

In the foregoing embodiment, the base absorbent body 10 functioned as the main body section, and the main body section had the absorbent body base material for absorbing fluid, but there is no limitation to this. For example, the main body section may be constituted by a fluid-impermeable member without including the absorbent body base material, and this fluid-impermeable member may be used for preventing fluid that has been absorbed by the absorbent body (the top absorbent body 20) from infiltrating into the undergarment 90.

The foregoing embodiment is merely for the purpose of elucidating the invention and is not to be interpreted as limiting the invention. The invention can of course be altered and improved without departing from the gist thereof, and any equivalents thereof are intended to be embraced therein.

The invention claimed is:

1. A sanitary napkin adapted to be worn by a user, said sanitary napkin comprising:
    a main body section; and
    an absorbent body including an absorbent member for absorbing fluid, and longitudinal direction, a width direction, and a thickness direction,
    wherein
    the absorbent body is superposed on the main body section on a user facing side,
    the absorbent body further includes
        a first end section joined to the main body section at a first joined section, and
        a second end section opposite to said first end section in the longitudinal direction
    and joined to the main body section at a second joined section, and
    a material length of the absorbent body between the first joined section and the second joined section is equal to or more than a material length of the main body section between the first joined section and the second joined section,
    the absorbent body includes a surface member that covers the absorbent member,
    the absorbent body includes a sealed section between the first joined section and the second joined section,
    the sealed section does not contain the absorbent member and has the surface member, and
    said sealed section defines a pick-up section that is adapted to be picked up by the user to adjust a position of the absorbent body for wearing.

2. The sanitary napkin according to claim 1, wherein the material length of the absorbent body between the first joined section and the second joined section is equal to or more than the material length of the main body section between the first joined section and the second joined section in a state where no force is externally applied to the absorbent article.

3. The sanitary napkin according to claim 1, wherein the material length of the absorbent body between the first joined section and the second joined section is equal to the material length of the main body section between the first joined section and the second joined section.

4. The sanitary napkin according to claim 1, wherein in the case where the user pulls up the sealed section to a side close to the second joined section when wearing the sanitary napkin, the sealed section is disposed closer to the second joined section than to the first joined section.

5. The sanitary napkin according to claim 4, wherein the main body section and the absorbent body are separable from each other between the first joined section and the second joined section, and
    the absorbent body further includes a fastening section that temporarily and releasably joins the absorbent body to the main body section between the sealed section and the first joined section.

6. The sanitary napkin according to claim 1, wherein the absorbent body comprises a front end section and a rear end section opposite to the front end section in the longitudinal direction, and
    the first joined section is arranged at the front end section and the second joined section is arranged at the rear end section.

7. The sanitary napkin according to claim 6, wherein the first joined section is sandwiched between the main body section and the absorbent body and extends from a front edge of the main body section rearwardly in the longitudinal direction.

8. The sanitary napkin according to claim 1, wherein the first joined section is elongated in the longitudinal direction, and the second joined section is elongated in the width direction.

9. The sanitary napkin according to claim 1, wherein a length of the first joined section in the longitudinal direction is greater than that of the second joined section in the longitudinal direction.

10. The sanitary napkin according to claim 1, wherein the absorbent body has a center region, which is adapted to face an bodily discharge opening of the user in use, and the first and second joined sections are outside of the center region.

11. The sanitary napkin according to claim 1, wherein said sealed section has a first sealed section having the surface member bonded to itself without the absorbent member; and a second sealed section having the surface member bonded to itself without the absorbent member, wherein the first sealed section is opposite to the second sealed section in the longitudinal direction.

12. The sanitary napkin according to claim 11, wherein a length of the second joined section in the longitudinal direction is less than that of the second sealed section in the longitudinal direction.

13. The sanitary napkin according to claim 11, wherein a length of the first sealed section in the longitudinal direction is less than that of the second sealed section in the longitudinal direction.

14. The sanitary napkin according to claim 11, wherein the second sealed section is adapted to be pulled up and to extend beyond a rear edge of the main body section in use.

15. The sanitary napkin according to claim 11, wherein the absorbent body further includes a fastening section between the first joined section and the second joined section, and the main body section and the absorbent body are temporarily releasably joined together at the fastening section and permanently joined together at the first and second joined sections.

16. The sanitary napkin according to claim 1, wherein the pick-up section comprises a first end directly connected with the second joined section and a second end opposite to the first end and adapted to be picked up by the user when pulling up the absorbent body.

17. The sanitary napkin according to claim 1, wherein the material length of the absorbent body between the first joined section and the second joined section is more than the material length of the main body section between the first joined section and the second joined section.

18. The sanitary napkin according to claim 1, wherein an entire length of the absorbent body in the longitudinal direction is equal to an entire length of the main body section in the longitudinal direction.

\* \* \* \* \*